US009481890B2

(12) United States Patent
Thomas et al.

(10) Patent No.: US 9,481,890 B2
(45) Date of Patent: Nov. 1, 2016

(54) MODIFICATION OF PLANT DEVELOPMENT AND MORPHOLOGY

(71) Applicant: British American Tobacco (Investments) Limited, London (GB)

(72) Inventors: Christopher John Robert Thomas, Cambridge (GB); Martin Richard Ward, Southampton (GB)

(73) Assignee: British American Tobacco (Investments) Limited, London (GB)

( * ) Notice: Subject to any disclaimer, the term of this patent is extended or adjusted under 35 U.S.C. 154(b) by 205 days.

(21) Appl. No.: 14/041,679

(22) Filed: Sep. 30, 2013

(65) Prior Publication Data

US 2014/0033364 A1 Jan. 30, 2014

Related U.S. Application Data

(63) Continuation of application No. 13/160,239, filed on Jun. 14, 2011, now Pat. No. 8,575,423, which is a continuation of application No. 11/729,514, filed on Mar. 28, 2007, now Pat. No. 8,093,459, which is a continuation of application No. PCT/GB2005/002719, filed on Sep. 28, 2005.

(30) Foreign Application Priority Data

Sep. 29, 2004 (GB) .................................. 0421598.4

(51) Int. Cl.
*C12N 15/87* (2006.01)
*C12N 15/82* (2006.01)

(52) U.S. Cl.
CPC ....... *C12N 15/8261* (2013.01); *C12N 15/8226* (2013.01); *C12N 15/8229* (2013.01); *C12N 15/8237* (2013.01); *C12N 15/8263* (2013.01)

(58) Field of Classification Search
None
See application file for complete search history.

(56) References Cited

U.S. PATENT DOCUMENTS

| | | | |
|---|---|---|---|
| 6,015,940 A | 1/2000 | Kaniewski et al. | |
| 6,180,406 B1 | 1/2001 | Stemmer | |
| 6,344,328 B1 | 2/2002 | Short | |
| 6,361,974 B1 | 3/2002 | Short et al. | |
| 8,093,459 B2 | 1/2012 | Thomas et al. | |
| 2002/0160378 A1* | 10/2002 | Harper ................. | C07K 14/415 435/6.14 |

FOREIGN PATENT DOCUMENTS

| | | |
|---|---|---|
| EP | 0120516 A2 | 2/1984 |
| EP | 0449375 A2 | 3/1991 |
| EP | 0583265 B1 | 4/1992 |
| EP | 0752008 B1 | 2/1995 |
| EP | 0866796 B1 | 9/1996 |
| EP | 1103606 A2 | 12/1996 |
| EP | 1138763 A2 | 12/1996 |
| NZ | 260511 | 7/1995 |
| WO | 8910396 A1 | 4/1989 |
| WO | 9117243 A1 | 5/1991 |
| WO | 9310251 A1 | 5/1993 |
| WO | 9720056 A2 | 6/1997 |
| WO | 9844138 A1 | 3/1998 |
| WO | 9960843 A1 | 5/1999 |
| WO | 0058517 A1 | 3/2000 |
| WO | 0134835 A2 | 5/2001 |
| WO | 0233106 A | 4/2002 |
| WO | 0233106 A2 | 4/2002 |
| WO | 0233107 A2 | 4/2002 |
| WO | 03008540 A | 1/2003 |

OTHER PUBLICATIONS

Lodge et al (1993, PNAS 90: 7089-7093).*
Gorschen et al (1997, Planta 202 (4): 470-478).*
Benfey et al (1989, EMBO J, 8(8):2195-2202).*
Benfey et al (1990, Science 250:959-966).*
Altschul et al. Gapped BLAST and PSI-BLAST: a new generation of protein database search programs. Nucleic Acids Res. 1997. 25(17):3389-3402.
Ausubel, F. M. Bent, R. Kingston, R. E. Moore, D. D. Seideman, J. G. Smith J. A. & Struhl K. Current protocols in molecular biology. New York: Greene and Willy Interscience. 1989. WorldCat (Bibliographic data for OCLC No. 16354867) pp. 1-3.
Baxevanis, A. D. Predictive Methods using DNA Sequences. In "Bioinformatics: A Practical Guide to the Analysis of Genes and Proteins." Editors A. D. Baxevanis and B. F. Ouellette. John Wiley and Sons Inc., New York. 2001. pp. 233-252.
Becker et al. New plant binary vectors with selectable markers located proximal to the left T-DNA border, Plant Molecular Biology. 1992. 20(6) pp. 1195-1197.
Benfey, P.N., and Chua, N-H. Regulated genes in transgenic plants. Science. 1989. 244:174-181.
Bevan, M. Binary Agrobacterium Vectors for Plant Transformation. Nucleic Acids Research. 1984. 12(22):8711-8721.

(Continued)

*Primary Examiner* — Stuart F Baum
(74) *Attorney, Agent, or Firm* — McKee, Voorhees & Sease, PLC

(57) ABSTRACT

A method of modifying morphology in a plant comprising introducing into a plant at least one chimaeric gene comprising a promoter sequence operably associated with a nucleic acid sequence, the promoter sequence being operable to direct expression in specific cells of the plant and the nucleic acid sequence encoding at least one gene product capable of altering the metabolism of or causing death of the specific cells and/or nearby cells. In particular, the promoter sequence is operable to direct expression in lateral bud or lateral shoot and the nucleic acid encoding at least one gene product capable of disrupting the metabolism of or causing the death of the lateral bud or lateral shoot or nearby cells. Preferably the promoter sequence comprises the sequence shown as SEQ ID No. 1 or SEQ ID No. 7 or SEQ ID No. 4, or a part thereof capable of regulating expression of a gene, or a sequence having at least 60%, preferably at least 75%, homology to SEQ ID No. 1 or SEQ ID No. 7 and being capable of regulating expression of a gene.

27 Claims, 18 Drawing Sheets

(56) References Cited

OTHER PUBLICATIONS

Christensen, A. H. & Quail, P. H. Ubiquitin promoter-based vectors for high level expression of selectable and/or screenable marker genes in monocotyledenous plants. Transgenic Research. 1996. 5:213-218.
Clough, S.J. & Bent, A.F. Floral dip: a simplified method for Agrobacterium-mediated transformation of Arabidopsis thaliana. Plant Journal. 1998. 16(6):735-743.
Cornejo et al. Activity of a maize ubiquitin promoter in transgenic rice. Plant Molec. Biol. 1993. 23:567-81.
Delaporta et al. A plant DNA Minipreparation: Version II. Plant Molecular Biology Reporter. 1983. 1(4):19-21.
Devereux et al. A comprehensive set of sequence analysis programs for the VAX. Nucleic Acids Res. 1984. 12(1):387-95.
Esau K. Anatomy of seed plants. New York & London. John Wiley & Sons Inc. 1960. pp. 2-24; Contents pp. ix-xvi; Index pp. 365-376.
Gatz, C. Novel inducible/repressible gene expression systems. Methods in Cell Biol. 1995. Chapter 30:411-424.
Horsch et al. A simple and general method for transferring genes into plants. Science. 1985. 227:1229-1231.
Jefferson, R.A. Assaying Chimeric Genes in Plants: The GUS Gene Fusion System. Plant Molec. Biol. Reptr. 1987. 5(1):387-405.
Kulikova et al. The EMBL Nucleotide Sequence Database. Nucleic Acids Res. 2004. 32:D27-30.
Mariani et al. Induction of male sterility in plants by a chimaeric ribonuclease gene. Nature 1990. 347:737-741.
Needleman SB, Wunsch CD. A general method applicable to the search for similarities in the amino acid sequence of two proteins. J. Molec. Biol. 1970. 48:443-53.
Odell et al. Identification of DNA sequences required for activity of the cauliflower mosaic virus 35S promoter. Nature. 1985. 313:810-812.
Sambrook et al. Molecular Cloning: A Laboratory Manual, 2nd edn. Cold Spring Harbor Laboratory Press, New York. 1989. Contents:v-xxxii.
Smith, T. and Waterman, M.S. Comparison of biosequences. Advances in Applied Mathematics. 1981. 2:482-489.
Stirpe, F. and Barbieri, T. Ribosome-inactivating proteins up to date. FEBS Lett. 1986. 195(1,2):1-8.
Warner SA, Scott R, Draper J. Isolation of an asparagus intracellular PR gene (AoPR1) wound-responsive promoter by the inverse polymerase chain reaction and its characterization in transgenic tobacco. Plant J. 1993. 3(2):191-201.
Zhang et al. Analysis of rice Act1 5' region activity in transgenic rice plants. Plant Cell 1991. 3:1155-65.
Database Genbank. Jun. 13, 2002, N. tabacum Sar8.2b protein gene, promoter region and complete cds., NCBI accession No. U64816. [Previously cited by or submitted to USPTO in U.S. Appl. No. 13/160,239, filed Jun. 14, 2011].
Database EMBL, Jan. 11, 2000, N. tabacum Sar8.2j gene, complete cds., accession No. U64812. [Previously cited by or submitted to USPTO in U.S. Appl. No. 13/160,239, filed Jun. 14, 2011].
Song, F., Goodman, R.M. (2002). Cloning and identification of the promoter of the tobacco Sar8.2b gene, a gene involved in systemic acquired resistance. Gene, 290 p. 115-124. [Previously cited by or submitted to USPTO in U.S. Appl. No. 13/160,239, filed Jun. 14, 2011].
International Search Report and Written Opinion, mailed Mar. 30, 2006, corresponding to PCT/GB2005/003719, filed Sep. 28, 2005. [Previously cited by or submitted to USPTO in U.S. Appl. No. 13/160,239, filed Jun. 14, 2011].
Benfey, et al. (1990) Science 250, p. 959-966. [Previously cited by or submitted to USPTO in U.S. Appl. No. 13/160,239, filed Jun. 14, 2011].
Benfey, et al. (1989) EMBO J. 8(8), p. 2195-2202. [Previously cited by or submitted to USPTO in U.S. Appl. No. 13/160,239, filed Jun. 14, 2011].
Smirnov, et al. (1997) Plant Physiology 114, p. 1113-1121. [Previously cited by or submitted to USPTO in U.S. Appl. No. 13/160,239, filed Jun. 14, 2011].
Gorschen et al. (1997) Planta 202 (4): 470-478. [Previously cited by or submitted to USPTO in U.S. Appl. No. 13/160,239, filed Jun. 14, 2011].
Altschul, Stephen F., et al, "Basic Local Alignment Search Tool", J. Mol. Biol., vol. 215, (1990), pp. 403-410. May 15, 1990.
An., G., et al, "New cloning vehicles for transformation of higher plants", The EMBO Journal, vol. 4, No. 2, (1985), pp. 277-284. Nov. 27, 1984.
An, G., et al, Gynheung, et al., "Binary vectors", Plant Molecular Biology Manual, A3, (1988), pp. 1-19. Jan. 1, 1988.
An, Gynheung, et al, "Transformation of Tobacco, Tomato, Potato and Arabisopsis thaliana Using a Binary Ti Vector System", Plant Physiology, vol. 81, (1986), pp. 301-305. Feb. 10, 1986.
Butcher, D.N., et al, "The Role of tissue culture in the study of crown-gall tumorigenesis", Tissue Culture Methods for Plant Pathologists, (1980), 6 pages. Jan. 1, 1980.
Caruthers, M.H., et al, "New chemical methods for synthesizing polynucleotides", Nucleic Acides Research, Symposium Series No. 7, IRL Press Limited, 1 Falconberg Court, London, W1V 5FG, UK, (1980), pp. 215-223. Jan. 1, 1980.
Christou, Paul, et al, "Genetic engineering of crop legumes and cereals: current status and recent advances", Agro Food Industry Hi-Tech, (Mar./Apr. 1994), pp. 17-27. Apr. 1, 1994.
NCBI, GenBan Submission AL096692.1, 20 pages, last accessed on May 5, 2016. May 5, 2016.
NCBI, GenBank Submission U64807.1, 1 page, last accessed on May 5, 2016. May 5, 2016.
NCBI, GenBank Submission U64808.1, 2 pages, last accessed on May 5, 2016. May 5, 2016.
NCBI, GenBank Submission U64809.1, 2 pages, last accessed on May 5, 2016. May 5, 2016.
NCBI, GenBank Submission U64810.1, 2 pages, last accessed on May 5, 2016. May 5, 2016.
NCBI, GenBank Submission U64811.1, 2 pages, last accessed on May 5, 2016. May 5, 2016.
NCBI, GenBank Submission U64813.1, 2 pages, last accessed on May 5, 2016. May 5, 2016.
NCBI, GenBank Submission U64814.1, 2 pages, last accessed on May 5, 2016. May 5, 2016.
Fraley, Robert T.. et al, "Genetic Transformation in Higher Plants", CRC Critical Reviews in Plant Sciences, vol. 4, Issue 1, (2011), pp. 1-47. Jun. 13, 2011.
Frame, Bronwyn R., et al, "Production of fertile transgenic maize plants by silicon carbide whisker-mediated transformation", The Plant Journal, vol. 6, No. 6, (1994), pp. 941-948. Aug. 12, 1994.
Henikoff, Steven, et al, "Amino acid substitution matrices from protein blocks", Proc. Natl. Acad. Sci., vol. 89, (1992), pp. 10915-10919. Nov. 1, 1992.
Hoekema, A., et al, "Non-onocogenic T-Region Derived Plant Vectors in the Agrobacterium Binary System", Department of Plant Molecular Biology, University of Leiden, Wassenaarsweg 64, 2333 Al Leiden, the Netherlands, (19840, pp. 62-71. Jul. 23, 1984.
Horn, Thomas, et al, Synthesis of oligonucleotides on cellulose., Nucleic Acids Research, Synposium Series No. 7, JKL Press Limited, 1 Falconberg Court, London, W1V 5FG, U.K., (1980), pp. 225-232. Jan. 1, 1980.
Karlin, Samuel, et al., "Applications and statistics for multiple high-scoring segments in molecular sequences", Proc. Natl. Sci. USA, vol. 90, (Jun. 1993), pp. 5873-5877. Jul. 1, 1993.
Karlin, Samula, et al., "Methods for assessing the statistical significance of molecular sequence features by using general scoring schemes", Proc. Natl Acad. Sci. USA, vol. 87, (Mar. 1990), pp. 2264-2268. Mar. 1, 1990.
Meyer, Peter, et al., "The use of African cassava mosaic virus as a vector system for plants", GENE, vol. 110, (1992), pp. 213-217. Aug. 12, 1991.
Morinaga, Yashushi, et al, "Improvement of Oligonucleotide-Directed Site-Specific Mutagenesis Using Doule-Stranded Plasmid DNA", Biotechnology, (Jul. 1984), pp. 636-639. Apr. 30, 1984.
Myers, Eugene W., et al., "Optimal alignments in linear space", Cabios, vol. 4, No. 1, (1988), pp. 11-17. Dec. 7, 1987.

(56) References Cited

OTHER PUBLICATIONS

Nelson, Richard M., et al, "A General Method of Site-Specific Mutagenesis Using a Modification of the Thermus aquaticus Polymerase Chain Reaction", Analytical Chemistry, vol. 180, (1989), pp. 147-151. Feb. 3, 1989.

Pearson, William R., et al., "Improved tools for biological sequence comparison", Proc. Natl. Acad. Sci., USA, vol. 85, (Apr. 1988), pp. 2444-2448. Sep. 17, 1987.

Institute of Plant Sciences, Swiss Federal Institute of Technology, "Gene Transfer to Plants: Assessment of Published Approaches and Results", Annual Review Plant Physio. Plant Mol. Bio., vol. 42, (1991), pp. 205-225. Jan. 1, 1991.

Styer, Lubert, "Biochemistry", table of contents, 3rd edition, (Stanford University, 1989), 4 pages Feb. 1, 1989.

Lodge, Jennifer K., et al., "Broad-spectrum virus resistance in transgenic plants expressing pokeweed antiviral protein", Proc. Natl. Acad. Sci., USA, vol. 9, (1993), pp. 7089-7093. Aug. 1, 1993.

European Patent Office, International Search Report and Written Opinion, Application No. PCT/GB2005/003719, filed Sep. 28, 2005, 5 pages.

\* cited by examiner

FIG. 1A

```
SEQ ID. No. 1     1 ------------------------------GCTATCAAGCTTTATT  16
                                                 : ::   ::: :::::
SEQ ID. No. 8   661 cttgtcttgtagtctattagcattgagtacatgtatccaagaacaaataagtaatatt 720

SEQ ID. No. 1    17 AAAGTGTCCAATAAGTGCAAGCCTATTAGTTGAAATGTCAAAAGTTGGTATCAAATTTAG  76
                    : : : :  : :: :  :  :::  : ::: ::: :: : ::  :  :: :::: :: :
SEQ ID. No. 8   721 gaagtat-c--taagagcaagcctattagttgaaatgacaaaggtataaaattttg    777

SEQ ID. No. 1    77 GGAGTTATTTATGCTCCCGTTTGGCCA---GATTTCGGTTACTATTTTTTAAGTTTAATTT 134
                    :  ::: ::: :::: :   ::: :::   :::: : :: ::::::  :::: :::
SEQ ID. No. 8   778 ggagttatttatgctcccgtttggcattggctacttgattttccaag-ttaaatt       836

SEQ ID. No. 1   135 GTTTTTTTCAAGTT-TC-----AA-GATTTATGACAGTTTTTGAGTGATATTTTTCCATTTA 188
                    ::::::::: :: : ::      :  :: ::::: :: :::  :: :::: :::::::
SEQ ID. No. 8   837 cttttttcaacttcccaaaaattgatttatgacattttttggataaaagtttt-tttcca   895

SEQ ID. No. 1   189 CTCACAAAACTTTAACTTTTTTTTCAAATAAAATACATGTACAAATACAATTTAATT 248
                    :: :::::: ::::  ::::: ::::::::: ::::: :: :: :::  :: :: ::
SEQ ID. No. 8   896 cctacaaaa-tttaacttcttttttcaaataaaatgcatgtccaaacacaacttcaact  954

SEQ ID. No. 1   249 TTCAAATATTATTTTCCAACATAACTTCAAAAACTCTTTTTTCAAGTGTTAATTAAATAT 308
                    :::::: :: ::::  :: :::: ::: :: ::::: :: :::::::: :::: :::::
SEQ ID. No. 8   955 ttcaaata-tattttttaacataactttcaaaaactcttttttcaagtttttaattatacat 1013
```

FIG. 1B

```
SEQ ID. No. 1    309  ATGTTTAACTATGTATTCATTTGTGCTTATGTTTTATCATGCATTTTCATAAGTGAATTT  368
SEQ ID. No. 8   1014  atgttcaactatgtattcatttctagttatg-tttatcacgca-tttcataagtgaattt  1071

SEQ ID. No. 1    369  CATACTCATCTTCATGCAAACACTTATACTATAAAGATATATTATTCCTATATACAACA   428
SEQ ID. No. 8   1072  catacttatcttcatgcaaacatatactatataaag--ata-ta-t--tat-t--c---c--  1120

SEQ ID. No. 1    429  TGTTTATACGAGATCATTACATTGTAAGTGTACCTTATTATTGGTAAATTTTGGACTTCA  488
SEQ ID. No. 8   1120  ------t-----a--aatac------a----a-c--------a----t-g-------  1133

SEQ ID. No. 1    489  CCAAAAATAATTAAGGAAGTAATGATATGCAATAAATAAATAAATAAAGTTAAAAA      548
SEQ ID. No. 8   1133  ------------tga-t----acg-a-g--at-c--------;                  1145

SEQ ID. No. 1    549  TATTATACTTGACTCAAGAGACACATTATGGGGAACACGWTTCTTTCACGATCCATCTTATC  608
SEQ ID. No. 8   1145  --------a---t-----aca-t--t---g---caa---------ct-g-----acctta--  1166

SEQ ID. No. 1    609  CTTTCATCGATAGAAGTTAGCAATAGCATTATTCTCATATTAGCCGGAATTATGGTTGTTT  668
SEQ ID. No. 8   1166  ---t--t--at-----ttt---ta--a--a--t--t--tt---gg----a---------  1184
```

FIG. 1C

```
SEQ ID. No. 1    669  GTCTCTTTATATGGTCATAGACTCTCGAGATAATTCATATTTCAAGACTAGTTATTTTTT  728
                      :       :   :       :  :::  :    :    :         :  :   ::::
SEQ ID. No. 8   1184  ----c-----t--tc----a--c-c-a-a-aa--atagtt---g---gg----tttt   1208

SEQ ID. No. 1    729  AGAGCTGAATTAAGTTTAAAAATTTATTTCTTCGTTCGAGCGTGCAAGGGTGTTAAGCAGG  788
                      : : ::  : :::      :::::: :::::    : :::::   :: :::::
SEQ ID. No. 8   1209  t------t--aatcga-tttg--attaattttcgttt---ggtgc----ggtttccgatt  1255

SEQ ID. No. 1    789  GGCTGAGGAAGAGCATTAGTCGCGGGTTCGAACGAACTCAGCTTAATTCTTATATTTGTA  848
                      ::  :  :       :::          :  : :::   :         ::  ::::::
SEQ ID. No. 8   1256  ggttt---gaacacccccta---tct--ggt-g---gta---ag-gtg--tcccacatttgt-  1298

SEQ ID. No. 1    849  TTAGAAAATACATAAAAATATGTATAAATATCTAATTACGAACATAATAACTAAGATAAAC  908
                      : ::                  :          ::  ::       :  ::
SEQ ID. No. 8   1299  tgaggg---------atgggtgtactatggtctt---gg--gcaa-gagttggagt---c  1341

SEQ ID. No. 1    909  TATGAGTTCCTGATAAATTGAAAATCTATAAACACCAAATCCTAGCTAGTCTCTGGTGTT  968
                      :      :    :                 :  ::    :   :  :  :: :::::::
SEQ ID. No. 8   1342  act-cgg--c-caccaatt----a--tct----a-cg---tcaa--gag--t-tggagtc  1378

SEQ ID. No. 1    969  AAGGTGTCCCACACATTTGTTGAGGGATGGGTTGTTATATGGTCTTGGGCAAGAGTTGGAGT  1028
                      :    :     :::                                :::::::::::::::
SEQ ID. No. 8   1379  act-cg--ccac------------------------------caattatctacgtcaagagttggagt  1413
```

FIG. 1D

```
SEQ ID. NO. 1    1029  CACTCGGCCACCAATTATCTATATTTGGCCCATTGTTTCCCATTAAAACAATTCCTCCCA  1088
                       :::::::::::  :::::::  ::::::::  ::::  :::::::::::::  :  :
SEQ ID. NO. 8    1414  cactcggccaccaattgtctacattgtgcccattgtttcccattaaaacaa-t--t--c-  1467

SEQ ID. NO. 1    1089  AGTTGATCTAGTTACTGTTCTCATTTATAATCCAAGTTGATACTATTTGTCATGTGGCTG  1148
                       :   :    :::  ::  :  :::::         ::::  :   ::::::::  ::
SEQ ID. NO. 8    1467  ------gccc------taa-g-------taaacaatccaaattgatacaatttgtcaagtggcca  1512

SEQ ID. NO. 1    1149  GCTATACGACACATTGTTTTTGTTTTT-TTGGAAAATTTCTAGGAAA-CCGTAGCCGCTT  1206
                       :   :  ::::::::::::  ::::::  ::::::   :::
SEQ ID. NO. 8    1513  tgta-acgacattgttttgttttttcttggaaagttcctagcaaacccgtagccacta   1571

SEQ ID. NO. 1    1207  CCATTCGGGTGTGCATTGATAACTAACTCACTGTGCAAATCACACAGAA  1266
                       :::   :::::: ::: ::: ::  ::::::::  ::::::: :::::
SEQ ID. NO. 8    1572  cccttcgggtgcgcacgggtaattcgctcactgtatattactcacaaga  1631

SEQ ID. NO. 1    1267  GATATAAATCGCATTAGGCACGCCCG--GT-ACG-A--C-TA-GGGGAGACTACTGGTG  1318
                       :::::::: :::::: ::  :::    :: :  :  :  :  :::::::::::: ::::
SEQ ID. NO. 8    1632  gatataaatcgcattaggtacacccgatatgacgaactctgactgaggagactgctagtg  1691

SEQ ID. NO. 1    1319  AGGAGAATCGATCTCAGATCTCCCATATGATAAACCACTCACCCAACTAACTCAATCAAC  1378
                       ::  :::::: :::: ::::  ::  :::: :::: :::::: ::  ::::: ::
SEQ ID. NO. 8    1692  agg-gaatccatctcaggtttcctatgtgggaaatcactcgcccaactaactcagtcta-  1749

SEQ ID. NO. 1    1379  CCCGGCGGGGVGTGACTTCACAGTAAGTC-TTTGTGAAGGCTTT--CTTTTTGTCA-TT  1435
                       :::  :       ::::  :::: :::::  ::::::::::::   ::::::  :
SEQ ID. NO. 8    1749  -cc--ttggcgtgcgtgactttaaagtaagtcttttgtgaaggcttttcctttttgtcattt  1807
```

FIG. 1E

```
SEQ ID No. 1   1436 TTCTCCCTTGTTTAGAACAAGTTGTTCTTGCACGAGAAACTATTAAGTYATATAAATAGG 1495
                        ::::::::::::::: :::  ::::::: ::              :
SEQ ID No. 8   1808 ttctcccttgttcagagcaagttg---tt--------c---------tataaatagg 1844

SEQ ID No. 1   1496 GGAGARACATTGTTTTCCTTTTTTACAGCAAAAAATTGRAACTCCAAATAGCTCA------TC 1551
                    ::::: ::::::: :::: ::::::::::::      :::::::::::::::::       ::
SEQ ID No. 8   1845 ggagaaacattattcccttttcacagcaaaaaattaaaactcgatatagctcatctttc 1904

SEQ ID No. 1   1552 AAAGGATCCTACTCG 1566
                    :::
SEQ ID No. 8   1905 aaa------------ 1907
```

FIG. 2A

| | | |
|---|---|---|
| SEQ ID. No. 9 | TATGCATATATTAAATCGCTTTCAATCAAATTTGTGTGCCTTGTTTTCTTTATAAAGAA | 14396320 |
| SEQ ID. No. 9 | TACAATTCAGCCTTCGTAGGAGCTGAGCTACGACATTGAAGATATTTTGGTCCGTACGTA | 14396260 |
| SEQ ID. No. 9 | TTACTATGGTTTAATAGGTTAAGTGACTATGAAAACGAAGACATTGTGTCGTAATCGTGT | 14396200 |
| SEQ ID. No. 4 | | 25 |
| | CGAAGACATTGTGTCGTAATCGTGT | |
| SEQ ID. No. 9 | GTAATTTCACTATCTTCCAAATAAAGAAATATATAATTGCTTCTTGAATCGGATGAGCT | 14396140 |
| SEQ ID. No. 4 | GTAATTTCACTATCTTCCAAATAAAGAAATATAATAATTGCTTCTTGAATCGGATGAGCT | 85 |
| SEQ ID. No. 9 | ACACGTTTTTAGATATTTCGCAACCTGTCTTCTTCGTTAGATCTAGGAAACATTGATTTA | 14396080 |
| SEQ ID. No. 4 | ACACGTTTTTAGATATTTCGCAACCTGTCTTCTTCGTTAGATCTAGGAAACATTGATTTA | 145 |
| SEQ ID. No. 9 | TAGAAATATGTTTCTATTATTTCTCTATTATTCATTCAACATGTTAATATCGCCACCACT | 14396020 |
| SEQ ID. No. 4 | TAGAATATGTTTTCTATTGTTTCTCTATTATTCATTCAACATGTTAATATCGCCACCACT | 205 |
| SEQ ID. No. 9 | CAAATATATTGACCATGTCAATTGTTTGATTGAACTATAAGTTTGATAAACAATTGTCAA | 14395960 |
| SEQ ID. No. 4 | CAAATATATTGACCATGTCAATTGTTTGATTGAACTATAAGTTTGATAAACAATTGTCAA | 265 |
| SEQ ID. No. 9 | ATTTATAAAAATTTAAAAGAGAAAATACATTTATATGAAAGAAAAAGAAAAGTGCAAAAAA | 14395900 |
| SEQ ID. No. 4 | ATTTATAAAAATTTAAAAGAGAAAAATGCATTTTATATGAAAGAAAAGAAAAGTGCAAAAAA | 325 |

FIG. 2B

```
SEQ ID. No. 9    GAAAGAACAAAGGATAAATGAGAGGTCGATTTTGTTTAGGAGGATATGGAATTGCTTCCA    14395840
SEQ ID. No. 4    GAAAGAACAAAGGATAAATGAGAGGTCGATTTTGTTTGTTTAGGAGGATATGGAATTGCTTCCA    385

SEQ ID. No. 9    AATTTAGCAAAGAAACATAAATGTTTTTGCCCCTATAAAGTCTTTAAACGTTATTCCAAA    14395780
SEQ ID. No. 4    AATTTAGCAAAGAAACATAAATGTTTTTGCCCCTATAAAGTCTTTAAACGTTATTCCAAA    445

SEQ ID. No. 9    TCTGTTCCAACATGTCCTCTTCATCCGACACATTTCTTATCCTCTTCTCTAATTTTTTTT    14395720
SEQ ID. No. 4    TCTGTTCCAACATGTCCTCTTCATCCGACACATTTCTTATCCTCTTCTCTAATTTTTTTT    505

SEQ ID. No. 9    GCTAAAAATTAAATCGAAAATTGAAAAACGAATTTTTGAGAACTATGTAAGATATTTTTT    14395660
SEQ ID. No. 4    GCTAAAAATTAAATCGAAAATTGAAAAACGAATTTTTGAGAACTATGTAAGATATTTTTT    565

SEQ ID. No. 9    CTTCCAATAACAACAAATTACCAAACAACTTTTTGTCGTTTTGTTACTAAATAAGTGGTA    14395600
SEQ ID. No. 4    CTTCCAATAACAACAAATTACCAAACAACTTTTTGTCGTTTTGTTACTAAATAAGTGGTA    625

SEQ ID. No. 9    CAATGAAATTATAAGTGATACAATAAAATCATTTGACTTAGATATAATAATATTCAAATT    14395540
SEQ ID. No. 4    CAATGAAATTATAAGTGATACAATAAAATCATTTGACTTAGATATAATAATATTCAAATT    685

SEQ ID. No. 9    AAAATGACAACAATACACCAATAAAATTATGAGAATTCTTCGAATCATATCAAAAATAAT    14395480
SEQ ID. No. 4    AAAATGACAACAATACACCAATAAAATTATGAGAATCTTCGAATCATATCAAAAATTAAT    745

SEQ ID. No. 9    TTTTTTTTTCGATAACAATAAATTATTAAACAACTTTTGTCGTAAGATTATTTTTTCC    14395420
SEQ ID. No. 4    TTTTTTTTTCGATAACAATAAATTATTAAACAACTTTTTGTCGTAAGATTATTTTTTCC    805
```

FIG. 2C

| | | |
|---|---|---|
| SEQ ID No. 9 | TGATAACAATAAATTATTAAATAATTTTCGATCGTTTTGTTGTTAGATAAATGATACAAT | 14395360 |
| SEQ ID No. 4 | TGATAACAATAAATTATTAATAATTTTCGATCGTTTTGTTGTTAGATAAATGATACAAT | 865 |
| SEQ ID No. 9 | GAATTCATTTCAACAACTTAGATACAACAATATTGGATCAAAATGAAAAATTATAAACAA | 14395300 |
| SEQ ID No. 4 | GAATTCATTTCAACAACTTAGATACAACAATATTGGATCAAAATGAAAATTATAAACAA | 925 |
| SEQ ID No. 9 | AGTATCATATATCTTTGTATCATATCAAAAACAAGATCATTTTTCCGATAACAATAAAT | 14395240 |
| SEQ ID No. 4 | AGTATCATATATCTTTGTATCATATCAAAAACAAGATCATTTTTTTCCGATAACAATAAAT | 985 |
| SEQ ID No. 9 | TATTAAACAACTTTTTGTCGTTTTGTTGCTAGATAAGTGAAACAATAAAATCATTTTGAC | 14395180 |
| SEQ ID No. 4 | TATTAAACAACTTTTTTGTCGTTTTGTTGCTAGATAAGTGAAACAATAAAATCATTTTGAC | 1045 |
| SEQ ID No. 9 | GAATTAGATATAACAATATTAAGATCACAATGAACAATAGTAAACAACAAATTATCAGAT | 14395120 |
| SEQ ID No. 4 | GAATTAGATATAACAATATTAAGATCACAATGAACAATAGTAAACAACAAATTATCAGAT | 1105 |
| SEQ ID No. 9 | ATTTTTGGTATTAAAAATAAGATTATTTTTCCGATAATAACAAATTATTAAACAATTTTT | 14395060 |
| SEQ ID No. 4 | ATTTTTGGTATTAAAAATAAGATTATTTTTCCGATAATAACAAATTATTAAACAATTTTT | 1165 |
| SEQ ID No. 9 | TATAGTTTTTGATGCTAAATAAGTGATATAATGAAATTGTTTTGACGATTTAGATACAATA | 14395000 |
| SEQ ID No. 4 | TATAGTTTTTGATGCTAAATAAGTGATATAATGAAATTGTTTTGACGATTTAGACACAATA | 1225 |
| SEQ ID No. 9 | ATATTAGGTTCAAAAATGACAATACTAAACAACAAATTATCAGATCATATCAAAAATAAAA | 14394940 |
| SEQ ID No. 4 | ATATTAGGTTCAAAAATGACAATACTAAACAACAAATTATCAGATCATATCAAAAATAAAA | 1285 |

FIG. 2D

```
SEQ ID. No. 9    TTATTTTTTTTCGATAACAGCAAATTATTAAACAACTTTTTTTTTAATTGCTAGATAAATGA    14394880
SEQ ID. No. 4    TTATTTTTTTTTCGATAACAGCAAATTATTAAACAACTTTTTTTTTTATTGCTAGATAAATGA   1345

SEQ ID. No. 9    TACAATAACCTCATTCGATATATATAATAATATTCAAATCAAAATGACAATAATAAACAA    14394820
SEQ ID. No. 4    TACAATAACCTCATTCGATATATATATAATAATATTCAAATCAAAATGACAATAATAAACAA   1405

SEQ ID. No. 9    TAAAATTATTATATTCAAATCATAATAAAAAATAAGACATACATCCAACGAATAATAAACAA   14394760
SEQ ID. No. 4    TAAAATTATTATTATATTGAATCATATATAAAAATAAGATACATGCAACGAATAATTAAACAA  1465

SEQ ID. No. 9    ACAAATTAAGTAATAAGGCAATGGATAGACTAATTAATGAAACTAAAACTGTGGATTATC    14394700
SEQ ID. No. 4    ACAAATTAAGTAATAAGGCAATGGATAGACTAATTAATGAAACTAAAACTGTGGATTATC    1525

SEQ ID. No. 9    TATTTGTCGTCTTTCGGAGAATCTAAACTTCGACCGACTTCAACGTATCTAATAATCCT    14394640
SEQ ID. No. 4    TATTTTGTCGTCTTTCGGAGAATCTAAACTTCGACCGACTTCAACGTATCTAATAATCCT    1585

SEQ ID. No. 9    AAAGTAACCTTACGCTCACAGTTCGGTTACTTTAAACTTCGTCAAAGTCATTTTGATAAA    14394580
SEQ ID. No. 4    AAAGTAACCTTACGCTCACAGTTCGGTTACTTTAAACTTCGTCAAAGTCATTTTGATAAA    1645

SEQ ID. No. 9    CGTCCACATCACGAAACGGTCCACGTACGTCCTATCTCGTGGATAAGTCTCCAGCCGCTGT   14394520
SEQ ID. No. 4    CGTCCACATCACGAAACGGTCCACGTACGTCTATCTCGTGGATAAGTCTCCAGCCGCTGT    1705

SEQ ID. No. 9    TTCACATGCTTATCTCACAGCTTTGTTACGATAACCTAGTCCTATGCTAATATCTTTAAC    14394460
SEQ ID. No. 4    TTCACATGCTTATCTCACAGCTTTGTTACGATAACCTAGTCCTATGCTAATATCTTTAAC    1765
```

FIG. 2E

| | | | |
|---|---|---|---|
| SEQ ID. No. 9 | CATAGTTAAATAATTTTAACCAAACCACGGCTTAAGTGTTTCAACTACATAAGTAGCTTTG | 14394400 |
| SEQ ID. No. 4 | CATAGTTAAATAATTTTTAACCAAACCACGGTTAAGTGTTTCAACTACATAAGTAGCTTTG | 1825 |
| SEQ ID. No. 9 | CCGGTGTATTACAAACAAGaacacaaacaaaaaaagaactctttcgtcgactaatgt | 14394340 |
| SEQ ID. No. 4 | CCGGTGTATTACAAACAAACAACACAAACAAAAAAAGAACTCTTTCGTCGACTAATGT | 1885 |
| SEQ ID. No. 9 | gatttattgttcaccggagtattaaagaagATGATGATCGGAGAAACTCGCAGGACTTAT | 14394280 |
| SEQ ID. No. 4 | GATTTATTGTTCACCGGAT | 1904 |
| SEQ ID. No. 9 | CCCACTGTTGAAATACCTCCATGGCCGGTACTTGAAGAGCTTACAACGTCGGAGTTTTT | 14394220 |
| SEQ ID. No. 9 | TCTCCGGTGATGAATAGTCCAGATTGTAGCATGCTTGAAGCTTTGGCGGGGTTGCAGCGT | 14394160 |
| SEQ ID. No. 9 | TATTTGCCGTCTAACGAACCCGATCCGGAGTCATACCCGGATCTATTGGGTCCGGATTCA | 14394100 |
| SEQ ID. No. 9 | CCAATCGATGCTTACTCATGCCACCATTTCCGTATGTACGATTTCAAAGTCAGGAGGTGT | 14394040 |
| SEQ ID. No. 9 | GCTCGTGGCCGGAGTCATGATTGGACGGAGTGTCCGTACGCTCATCCCGGAGAAAAAGCT | 14393980 |
| SEQ ID. No. 9 | CGCCCGGAGAGATCCGAGGAAGTACCATTACTCTGGTACGCTTGTCCTGATTTTCGTAAA | 14393920 |
| SEQ ID. No. 9 | GGTGGCTGCAAGAAGGTGACTCTTGTGAGTTTGCTCATGTGTTTTCGAGTGTTGGCTT | 14393860 |

FIG. 2F

| | | |
|---|---|---|
| SEQ ID. No. 9 | CATCCAGTTCGTTACCGTACTCAGCGTGTAAAGACGGTGGTAACTGTCTCCGGAAAATT | 14393800 |
| SEQ ID. No. 9 | TGTTTCTTTGCTCATTCACCGGATCAGCTTAGGTTTTTACATACTCGGAGCCCTGACAGA | 14393740 |
| SEQ ID. No. 9 | GTTGATTCTTTTGACGTTTCGTCTCCGATTCGTGCTAGAGCATTCAGCTGTCGATTTCT | 14393680 |
| SEQ ID. No. 9 | CCGGTTTCTGGTTCGCCCACCGATGAGTCCAAGAGCTGACTCGGAGTCTCTCCGATGACT | 14393620 |
| SEQ ID. No. 9 | CAGTCACTGAGTCGATCTCTCGGGTCTTGTTCGATAAACGACGTCGTTCCTTCGTTTAGG | 14393560 |
| SEQ ID. No. 9 | AATTTACAGTTTAATTCGGTAAAATCATTTCCTCGTAACAATCCTTTATTCGGATTCGGG | 14393500 |
| SEQ ID. No. 9 | TCGCCCCGTGGATCGATCTTGGGTCCTGGGTTTCAGTCTCTGCCTACAACACCGACCCGA | 14393440 |
| SEQ ID. No. 9 | CCAAGGGAATCTGGATATCTTGGATATTTGGGAGTATGGTTTGGAGGAAGAACCCGTAATGGAGCGTGTC | 14393380 |
| SEQ ID. No. 9 | GTTGAGTCGGGTCGTGAGCTACGAGAGAAAAGATGCGCGAGAAACTGCACAAGGAGAATTGC | 14393320 |
| SEQ ID. No. 9 | ATGGATCGAGTTGCCCAGGATCCGATCAGAATTTGGGTGAGGCTCCTGATGTCGGGTGG | 14393260 |
| SEQ ID. No. 9 | GTATCTGACCTGCTCATG TAA agaaaaaaatctgaccgtatttcgaagtctcattggctt | 14393200 |
| SEQ ID. No. 9 | tttggatatcttccaaggaaagaggaggatcttagtgtgttcatatattattt | 14393140 |

FIG. 2G

| | | | |
|---|---|---|---|
| SEQ ID. No. 9 | actaatctcgtatttatctgctaataagaattaattatggattttggggcctgattttt | 14393080 |
| SEQ ID. No. 9 | ctaagatgatcgttgtatagatgtgcccttaggtttaattatgaaatagtattaatata | 14393020 |
| SEQ ID. No. 9 | atcgtgttatataagactataatgttagattgtaaccacttgtactaatctatgaatga | 14392960 |
| SEQ ID. No. 9 | atgcaaattattatct | 14392944 | a b c d e

MODIFICATION OF PLANT DEVELOPMENT AND MORPHOLOGY

CROSS-REFERENCE TO RELATED APPLICATIONS

This application is a continuation of and claims priority under 35 U.S.C. §120 to U.S. Non-Provisional patent application Ser. No. 13/160,239, filed Jun. 14, 2011, now U.S. Pat. No. 8,575,423 issued Nov. 5, 2013 and entitled "Modification of Plant Development and Morphology," which is a continuation of and claims priority under 35 U.S.C. §120 to U.S. Non-Provisional patent application Ser. No. 11/729,514, filed Mar. 28, 2007, now U.S. Pat. No. 8,093,459 issued Jan. 10, 2012 and entitled "Modification of Plant Development and Morphology," which is a continuation of international PCT application Serial No. PCT/GB2005/003719 filed Sep. 28, 2005 and published as WO2006/035221 in English on Apr. 6, 2006, which claims priority under 35 U.S.C. §119 to Great Britain Application 0421598.4 filed on Sep. 29, 2004. The entire contents of the aforementioned applications are herein expressly incorporated by reference.

This application hereby incorporates by reference the sequence listing in the text file, named "BTMK-024_02US_318520-2360_TEXT.txt," filed herewithin and having a size of 15 KB.

FIELD OF THE INVENTION

The invention relates to a method for modifying the development and morphology of a plant. The invention further relates to the use of a DNA sequence to regulate exogenous gene expression in tissues of a plant. The invention yet further relates to an identified DNA sequence which act as an promoter which is operable to direct expression in specific cells of a plant.

BACKGROUND

The control of plant morphology is of major importance in the commercial production of plants for agricultural or horticultural purposes, to enhance productivity and yield, to improve the efficiency of husbandry and harvest, and to achieve aesthetic desirability. Features which require control or modification may include the morphology of the flower, fruit or tuber, the quantity of flowers, fruit, seed or tubers, the extent of primary and lateral roots, the form of the aerial shoots or trunk, and the presence of thorns or stinging hairs. Other features which may be desirably controlled include the advancement or delay of abscission of leaves, flowers or fruit, the release of seeds, and the production of storage organs or secretory glands.

Morphological changes often occur as a result of environmental impact on the plant, including physical damage, herbivore predation, pathogen infection, cold, heat, and drought. They can often be brought about deliberately by human intervention, either physically (pruning, bending, tying, staking, or excising particular organs or structures) or chemically (application of agrochemicals and plant growth substances). Whichever is the causative agent, morphological changes are enacted by expression of genes within the cells of the plant itself. At the onset of the change, the initiation of expression of one or more genes occurs in those particular tissues where cell growth, proliferation, development or necrosis is required to culminate in the gross physical change.

The expression of a gene is dependent upon its DNA sequence being transcribed into RNA by the action of RNA polymerase. To achieve this, RNA polymerase must recognise and attach to a region of DNA sequence located upstream of (i.e. 5' to) the gene coding sequence in order for transcription to be initiated. Such a region is termed the promoter of the gene. The intrinsic nature of the promoter sequence determines the circumstances and the manner in which the gene is expressed.

There are, broadly speaking, four types of promoters found in plant tissues; constitutive, tissue-specific, developmentally-regulated, and inducible/repressible, although it should be understood that these types are not necessarily mutually exclusive.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell et al, 1985), the rice actin 1 gene (Zhang et al, 1991) and the maize ubiquitin 1 gene (Cornejo et al, 1993).

A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Examples of tissue-specific promoters known in the art include those associated with the patatin gene expressed in potato tuber and the high molecular weight glutenin gene expressed in wheat, barley or maize endosperm.

A developmentally-regulated promoter directs a change in the expression of a gene in one or more parts of a plant at a specific time during plant development. The gene may be expressed in that plant part at other times at a different (usually lower) level, and may also be expressed in other plant parts.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner et at (1993), temperature response as disclosed by Benfey & Chua (1989), and chemically induced, as described by Gatz (1995).

A promoter sequence may comprise a number of defined domains necessary for its function. A first of these comprises approximately 70 base pairs located immediately upstream of (that is, 5' to) the structural gene and forms the core promoter. The core promoter contains the CAAT and TATA boxes and defines the transcription initiation site for the gene. A series of regulatory sequences upstream of the core promoter constitute the remainder of the promoter sequence and determine the expression levels, the spatial and temporal patterns of expression, and the response to inducers. In addition some promoters contain sequence elements which act to enhance the level of expression, for example that from the pea plastocyanin promoter as described in International Patent Publication No. WO 97/20056.

Genetic modification of plants depends upon the introduction of chimaeric genes into plant cells and their controlled expression under the direction of a promoter. Promoters may be obtained from different sources including animals, plants, fungi, bacteria, and viruses, and different promoters may work with different efficiencies in different tissues. Promoters may also be constructed synthetically.

It may often be desirable to express introduced genes in a number of different tissues within a plant. For example the expression of a resistance to a pathogen or pest, or tolerance to temperature extremes might be best expressed throughout all tissues in a plant. Similarly it might be desirable to ensure the expression of the transgenes at all times throughout the development of the plant. Also, a promoter which is expressed in a manner that is immune to the influence of inducers or repressors resulting from unforeseen environmental stimuli may also be useful to ensure the continued expression of a trait. For these purposes, the use of a "constitutive" promoter would be desirable. Examples of constitutive promoters include the CaMV 35S promoter. For cereals the ubiquitin promoter is a constitutive promoter of choice (Christensen & Quail, 1996).

However, in some instances it is more desirable to control the location of gene expression in a transgenic plant. This may enhance the effect of gene expression by ensuring that expression occurs preferentially in those tissues where the effect of the gene product is most efficacious. By the same argument, modulated expression can reduce potential yield loss by limiting the resource drain on the plant. Further advantages include limiting the expression of agronomically useful yet generally deleterious genes to specific tissues by localisation and compartmentalisation of gene expression in cases where the gene product must be restricted to, or excluded from, certain tissues. For example, anther specific expression of the suc inhibitor genes (Mariani et al, 1990) has been used in male sterility systems, whereas expression in other parts of the plant would result in toxicity. A similar cell death system is described in International Patent Application WO 89/10396 where an RNAse protein is used in combination with an anther specific promoter to cause necrosis of the anther cells and confer male sterility on the plant.

In International Patent Applications WO 02/33106 and WO 02/33107 are described plant cell death systems providing resistance to nematode infection by the expression of a ribosome inactivating protein (Maize Ribosome Inactivating Protein, Pokeweed Antiviral Protein) under the regulation of nematode feeding site specific promoters. In these cases the specificity of expression of the deleterious gene is enhanced by the promoters being both tissue specific and responsive to nematode invasion.

In some instances two or more transgenes may be expressed in a plant in similar or different locations. Each transgene may be expressed under the control of a different promoter which expresses in more than one region of the plant. The promoters may be selected so that there is an overlap in their respective expression sites at one or more desired locations. This overlap site(s) gives increased specificity and targeting of gene expression. By judicious selection of the gene product encoded by each transgene, the overlapping expressing of both transgenes may lead to an additive or enhanced effect on the target tissues, whereas expression of only one or other of the transgenes at other locations may cause no effect on the plant. For example in International Patent Application WO 02/33106 two separate peptide domains derived from Maize Ribosomal Inhibitory Protein (RIP) are expressed under the regulation of two different tissue specific promoters, having different expression profiles but which nevertheless have one site in common, resulting in the production of an active protein at the site of overlap.

Conversely, the two transgenes may encode an effector molecule and an agonist molecule or protectant. In this case, the effector molecule will affect the plant at all locations where it is expressed, except those where the expression site overlaps with that of expression of the agonist or protectant molecule. In NZ 260511 a plant cell death system is proposed with increased tissue specificity. This system comprises the expression of a cytotoxic molecule (under the control of a first promoter, which first promoter causes expression in specific target cells and at one or more other sites in the plant), in conjunction with a protective molecule (under the control of a second promoter, which second promoter causes expression in all of the sites where the first promoter is active except the specific target cells). Examples of suitable cytotoxic and protective molecules are proteases and protease inhibitors, respectively, or nucleases and nuclease inhibitors, respectively. WO 93/10251 discloses the use of a cytotoxic ribonuclease molecule Barnase together with the protective inhibitor molecule Barstar.

Another example of a two-component transgenic system is provided in International Patent Application No. WO98/44138. This system comprises the expression of a gene product under the control of a promoter, which promoter and gene product are selected so that there is an overlap in their respective expression and effector sites at a desired location. The promoter directs expression in the specific cells and also at one or more other sites in the plant, whilst the molecular target of the gene product occurs in a second range of cells also including the specific target cells. This overlap site(s) gives increased specificity and targeting of gene expression to the cells at the desired location. By judicious selection of the gene product encoded by the transgene, the expression in non-target cells causes no effect on the plant.

A major application of the localised expression of a deleterious gene to a particular tissue, would be in the modification of plant morphology, for example by the controlled necrosis or prevention of development of certain tissues or organs, such as flowering structures, fruiting bodies, storage tissues, shoots, leaf tissues, root tissues, abscission zones, secretory glands, stinging cells, trichomes, or thorns.

A particular application of localised expression of a deleterious gene to modify plant morphology would be in the prevention of lateral shoot outgrowths from leaf axillary meristems. The anatomy of axillary meristems and lateral buds is described in Esau (1960). Outgrowth of lateral shoots most commonly arises when the dominance of the apical shoot is removed or reduced; for example when the apical shoot is damaged or removed, either accidentally through physical damage or predation by herbivores, or as part of agricultural practice e.g. coppicing. Other changes which modify for example the production, transport, detection, or metabolism of endogenous plant growth substances may also cause outgrowth from axillary meristems. Lateral shoots, or "suckers", may be undesirable for purely aesthetic reasons, may produce a plant with unusable morphology, or may have a detrimental metabolic effect on the plant as a whole by acting as an additional source or sink for various metabolites or plant growth substances.

One example where lateral bud outgrowth occurs is in the commercial cultivation of tobacco, where the apical shoot comprising the inflorescence and uppermost leaves is removed at a specific time during the growth of the plant, in a process named "topping", to stimulate growth and development of the remaining leaves, to enhance root growth, and to encourage the redistribution of metabolites and secondary compounds to the plant leaves. A drawback to the topping process is that it also stimulates the outgrowth of lateral shoots which thereby offsets the desired redistribution of metabolites. This effect is commonly overcome by the physical removal of the lateral shoots which is highly labour intensive or by the application of chemical shoot suppressants such as maleic hydrazide, which is both costly in terms of materials and may result in the retention of chemical residues on the harvested plant. A system which prevents such "suckering" by specifically directing the disruption of those cells involved in lateral bud outgrowth, would therefore provide a great benefit to the cultivation of tobacco.

Ribosome inactivating proteins (RIPs) are a group of toxic plant proteins that catalytically inactivate eukaryotic ribosomes (Stirpe and Barbieri 1986). RIPs function as N-glycosidases to remove a specific adenine in a conserved loop of the large rRNA, and thereby prevent binding of Elongation Factor 2, thus blocking cellular protein synthesis. Three forms of RIPs have been described. Type 1 RIPs such as pokeweed antiviral protein and barley translation inhibitor are each comprised of a single polypeptide chain, each with an approximate $M_r$ value of 30,000. Type 2 RIPs such as ricin, abrin and modeccin each comprise two polypeptide chains, one with RIP activity linked by a disulphide bond to the other galactose-binding lectin chain. Type 3 RIPs such as maize RIP comprise a single polypeptide chain which subsequently undergoes proteolytic cleavage to release two active peptide domains.

Pokeweed (*Phytolacca americana*) produces three distinct antiviral proteins, namely PAP', PAPII and PAP-S that appear in spring leaves, summer leaves and seeds, respectively. Amino acid similarities between these three proteins have been observed. As used herein 'PAP' covers all three of these antiviral proteins.

U.S. Pat. No. 6,015,940 discloses the preparation of a cDNA clone of PAP' prepared from spring leaves of pokeweed, and the use thereof under the control of a constitutive promoter (either cauliflower mosaic virus 35S promoter or the figwort mosaic virus 35S promoter) in the production of transgenic tobacco and potato plants resistant to infection by the viruses PVX and PVY.

Transgenic plants containing the summer leaf form of PAP, PAP-II, have been described in WO 99/60843. A number of full length and truncated PAP-II gene sequences were screened in order to identify those variant PAP-II proteins which retained antiviral activity but exhibited no phytotoxicity. Transgenic plants exhibited both antiviral and antifungal activity.

The PAP gene is expressed in vivo in leaves initially to produce an inactive Pro-PAP protein. It is known that following translation, the Pro-PAP' protein molecule is targeted to the cell wall. At some stage during this process the N- and C-terminal extensions of the Pro-PAP' molecule are cleaved to produce an activated PAP' molecule (mature PAP'). In the case of PAP-S (expressed in seeds) the cellular localisation is not known. However, the N-terminal processed region of PAP-S appears to have properties similar to signal sequences for targeting.

The structure of the mature PAP-S protein, i.e. with N- and C-terminal extensions removed, may be described in terms of two separate domains, corresponding to the two domains of Type 3 RIPs, or the two polypeptides of Type 2 RIPs, i.e. the ribosome binding domain and the catalytic domain.

SUMMARY OF THE INVENTION

In one aspect the present invention provides a method of modifying morphology in a plant comprising introducing into a plant at least one chimaeric gene comprising a promoter sequence operably associated with a nucleic acid sequence, the promoter sequence being operable to direct expression in specific cells of the plant, and the nucleic acid sequence encoding at least one gene product capable of altering the metabolism of the specific cells and/or nearby cells.

In one embodiment the gene product may be capable of enhancing the metabolism of or promoting vigour of the specific cells and/or nearby cells.

In another preferable embodiment, the gene product is capable of disrupting the metabolism of or causing death of the specific cells and/or nearby cells.

In a further aspect the present invention provides a method of modifying morphology in a plant comprising introducing into a plant at least one chimaeric gene comprising a promoter sequence operably associated with a nucleic acid sequence, the promoter sequence being operable to direct expression substantially specifically in a lateral bud and/or lateral shoot, preferably a lateral bud initiation cell, and the nucleic acid encoding at least one gene product capable of altering the metabolism of the lateral bud and/or lateral bud initiation cells and/or nearby cells.

In one embodiment the gene product may be capable of enhancing the metabolism of or promoting vigour of the specific cells and/or nearby cells.

In another preferred embodiment, the gene product is capable of disrupting the metabolism of or causing death of the specific cells and/or nearby cells.

The term "substantially specifically" as used herein means that the promoter according to the present invention is operable to direct expression predominantly in the lateral bud and/or lateral shoot. The promoter according to the present invention may in addition to being operable to direct expression in the lateral bud and/or lateral shoot may also be operable to direct expression in other cell type(s) or tissue(s) within the plant provided that the predominant expression (i.e. greater than at least 51% of the overall (total) expression in the plant) occurs within the lateral bud and/or lateral shoot.

The promoter according to the present invention may in addition to being operable to direct expression in the lateral bud and/or lateral shoot may also be operable to direct expression in other cell type(s) or tissue(s) within the plant provided that the overall expression in the plant only affects (or significantly affects) outgrowth from meristems.

The promoter according to the present invention may in addition to being operable to direct expression in the lateral bud and/or lateral shoot may also be operable to direct expression in other cell type(s) or tissue(s) within the plant provided that the overall expression does not kill the plant.

Preferably, the term "substantially specifically" as used herein means that the promoter according to the present invention is operable to direct expression predominantly in lateral buds and/or lateral shoots of a plant such that, for instance, a nucleic acid sequence operably associated with said promoter is expressed predominantly in lateral buds and/or lateral shoots with less than 50%, preferably less than 25%, preferably less than 10%, more preferably less than 5% of the overall expression level of said nucleic acid sequence being in any other plant tissue or cell of the plant.

For example, a nucleic acid sequence expressed under the control of the promoter according to the present invention may be predominantly expressed in the lateral bud and/or lateral shoot with less than 25%, preferably less than 10%, more preferably less than 5% of the overall expression level in any other tissue.

The promoter sequence may comprise the sequence shown in SEQ ID No.1, SEQ ID No. 7 or SEQ ID No.4, or a functional part thereof, or a sequence having at least 60% identity thereto.

Preferably the promoter sequence is the sequence shown in SEQ ID No.1, SEQ ID No. 7 or SEQ ID No.4, or a functional part thereof, or a sequence having at least 60% identity thereto.

Preferably, the promoter sequence comprises the sequence shown in SEQ ID No.1 or a functional part thereof or a sequence which is at least 75%, preferably at least 80%, preferably at least 90%, preferably at least 97%, identical thereto.

Preferably, the promoter sequence comprises the sequence shown in SEQ ID No. 7 or a functional part thereof or a sequence which is at least 75%, preferably at least 80%, preferably at least 90%, preferably at least 97% identical thereto.

In one embodiment of the invention the morphology of a plant is affected by one or more gene products, preferably one gene product.

In a further embodiment of the invention the morphology of a plant is affected by two or more gene products. Preferably the nucleic acid sequence encodes two or more gene products. Thus, by way of example only one chimaeric gene may be introduced into the plant, which chimaeric gene comprises a nucleic acid sequence encoding two or more gene products. Alternatively two or more chimaeric genes may be introduced into the plant, each chimaeric gene comprising a nucleic acid sequence encoding a gene product. By way of example only, two or more chimaeric genes may be introduced into the plant, each chimaeric gene comprising a nucleic acid sequence encoding one or more gene products. Thus, for example, one chimaeric gene may comprise a nucleic acid sequence encoding one gene product and a further chimaeric gene may comprise a nucleic acid sequence encoding multiple gene products, i.e. 2, 3 or 4 gene products. Alternatively, both chimaeric genes may comprise nucleic acid sequence(s) encoding multiple gene products. Preferably the two or more gene products function independently of each other to effect disruption of the metabolism of the cells by an additive effect. Alternatively the two or more gene products interact with each other to effect disruption of the metabolism of the cells by a synergistic or by an antagonistic effect.

Preferably the outgrowth of lateral shoots is modified. The outgrowth of lateral shoots may be enhanced. Suitably the outgrowth of lateral shoots may be prevented or reduced and/or delayed.

Preferably the outgrowth of lateral shoots is modified by disrupting metabolism or by causing death of cells involved in lateral bud development.

Cells involved in the lateral bud development may include those of the pro-meristem, protoderm, epidermis, stomata, guard cells, endodermis, periderm, cortex parenchyma, stinging cells, storage cells, ovule endosperm, pollen, abscission zone, trichomes, secretory cells, phellem, phellogen, phelloderm, procambium, cambium, protoxylem, xylem, rays, protophloem, phloem, collenchyma, parenchyma, chlorenchyma, tunica, corpus, cortex, prophyll structures, and foliar structures.

The term "specific cells" as used herein is intended to mean those cells in which the promoter is predominantly expressed, preferably those cells in which the promoter is expressed substantially specifically.

The term "specific cells of the plant" includes lateral bud and/or lateral shoot cells, i.e. those cells involved in lateral bud initiation and/or development. In one embodiment preferably the "specific cells of the plant" are the lateral bud and/or lateral shoot cells.

In one embodiment the specific cells of the plant may be a cell of one or more of the: pro-meristem, protoderm, epidermis, stomata, guard cells, endodermis, periderm, cortex parenchyma, stinging cells, storage cells, ovule endosperm, pollen, abscission zone, trichomes, secretory cells, phellem, phellogen, phelloderm, procambium, cambium, protoxylem, xylem, rays, protophloem, phloem, collenchyma, sclerenchyma, parenchyma, chlorenchyma, tunica, corpus, cortex, prophyll structures, and foliar structures.

The term "predominantly expressed" as used herein means that the promoter according to the present invention is operable to mainly (i.e >51% of the total expression) direct expression in the specific cells of the plant (such as the later bud and/or lateral shoot cells), although lower levels of expression may be found in other cell type(s) or tissue(s).

For example, it has been found that the promoter according to the present invention is operable to predominantly direct expression in the lateral bud and/or lateral shoot but that there may also be expression in another tissue or cell type. For example, there may also be expression in wound tissue and/or stem and/or leaf tissue.

Suitably the outgrowth of the lateral bud or lateral shoot may be prevented or reduced and/or delayed. Preferably the outgrowth of the lateral bud or lateral shoot is modified by disrupting metabolism or by causing death of cells involved in lateral bud and/or lateral shoot development.

The term "lateral bud tissue" as used herein includes lateral bud cells and/or lateral shoot cells.

Preferably the gene product of the nucleic acid sequence capable of disrupting the metabolism or of causing death of specific cells and/or nearby cells is a deleterious product, suitably a cytotoxic molecule.

Preferably the gene product of the nucleic acid sequence capable of disrupting the metabolism or of causing death of specific cells and/or nearby cells is a ribosome inactivating protein (RIP) or a variant or functional part thereof. For example, the RIP may be a Type 1 RIP and/or a Type 2 RIP and/or a Type 3 RIP or a variant or functional part thereof. Preferably the gene product is a pokeweed antiviral protein (PAP) or a variant or functional part thereof. The gene product may be PAP' or PAPII or a variant or functional part thereof. More preferably the gene product is pokeweed antiviral protein S (PAP-S) or a variant or functional part thereof.

The present invention also provides a nucleic acid comprising a promoter sequence, the promoter sequence being as shown in SEQ ID No. 1, or functional part thereof, or a sequence having at least 65% identity thereto, more preferably at least 75% identity thereto, more preferably at least 85% identity thereto, more preferably at least 95% identity thereto, more preferably at least 97% identity thereto, more preferably at least 98% identity thereto, most preferably at least 99% identity thereto and being capable of regulating expression of a gene.

The present invention also provides a nucleic acid comprising a promoter sequence, the promoter sequence being as shown in SEQ ID No. 7, or functional part thereof, or a sequence having at least 65% identity thereto, more preferably at least 75% identity thereto, more preferably at least 85% identity thereto, more preferably at least 95% identity thereto, more preferably at least 97% identity thereto, more preferably at least 98% identity thereto, most preferably at least 99% identity thereto and being capable of regulating expression of a gene.

The present invention also provides a chimaeric gene comprising a promoter sequence operably associated with a nucleic acid sequence the promoter sequence being as shown in SEQ ID No. 1, or functional part thereof, or a sequence having at least 65% identity thereto more preferably at least 75% identity thereto, more preferably at least 85% identity thereto, more preferably at least 95% identity thereto, more preferably at least 97% identity thereto, more preferably at least 98% identity thereto, most preferably at least 99% identity thereto and being capable of regulating expression of a gene.

The present invention also provides a chimaeric gene comprising a promoter sequence operably associated with a nucleic acid sequence the promoter sequence being as shown in SEQ ID No. 7, or functional part thereof, or a sequence having at least 65% identity thereto, more preferably at least 75% identity thereto, more preferably at least 85% identity thereto, more preferably at least 95% identity thereto, more preferably at least 97% identity thereto, more preferably at least 98% identity thereto, most preferably at least 99% identity thereto and being capable of regulating expression of a gene.

The present invention also provides a chimaeric gene comprising a promoter sequence operably associated with a nucleic acid sequence the promoter sequence being as shown in SEQ ID No. 4, or a functional part thereof, or a sequence having at least 65% identity thereto and being capable of regulating expression of a gene.

Preferably the nucleic acid sequence and/or the nucleic acid according to the present invention and/or the chimaeric gene according to the present invention is a DNA sequence.

In one embodiment the chimaeric gene according to the present invention is obtainable, preferably obtained, from the clone pBNP 085-0501-001 (NCIMB 41343).

Preferably the nucleic acid sequence is capable of regulating expression of an additional sequence. Suitably the additional sequence encodes a protein or RNA, a cosuppression sequence, an antisense sequence or a dsRNA (double-stranded RNA) inhibition sequence.

Preferably the additional sequence is obtainable, preferably obtained, from a plant. The plant may be a member of the family Solanaceae. Preferably the plant may be a member of the subfamily Cestroideae. More preferably the plant is one or more of tomato, potato, aubergine, *Petunia* or tobacco. More preferably the plant is from the genus *Nicotiana*. Most preferably the plant is *Nicotiana tabacum*.

It is preferred that the additional sequence is capable of disrupting the metabolism of or causing death of the specific cells and/or nearby cells. It is preferred that the additional sequence encodes a pokeweed antiviral protein or functional part thereof.

The nucleic acid sequences and/or nucleic acid and/or the chimaeric gene referred to herein may be isolated sequences or, alternatively, may be synthesised sequences.

The present invention further provides a recombinant DNA comprising vector DNA and a nucleic acid sequence according to the present invention and/or a nucleic acid according to the present invention and/or a promoter sequence according to the present invention and/or a chimaeric gene according to the present invention. The recombinant DNA may suitably further comprise a coding sequence of a gene. Preferably the vector DNA comprises a plasmid, cosmid, virus or phage. Suitably the recombinant DNA may comprise a promoter to direct expression of a selectable marker gene.

Preferably the recombinant DNA resides in a host cell. Suitably the host cell may allow transcription and translation of the recombinant DNA.

The present invention further provides a plant produced according to the method of the present invention. The present invention further provides a genetically-engineered plant comprising a nucleic acid sequence and/or a nucleic acid and/or a promoter sequence and/or a chimaeric gene according to the invention. Preferably the nucleic acid and/or a promoter sequence is operably associated with a coding sequence of a gene.

According to a further aspect of the present invention there is provided a plant comprising a recombinant DNA according to the present invention. The plant according to the present invention may be of interest to the horticulture industry, the floriculture industry, the forestry industry and/or the agriculture industry. The plant may be a plant which is grown for the purpose of providing cut flowers. The plant may be tomato, cucumber, *Petunia, Dianthus, Picea, Pinus, Eucalyptus, Populus*, a dicotyledonous species such as potato, tobacco, cotton, lettuce, eggplant, melon, squash, pea, canola, soybean, sugar beet or sunflower, or a monocotyledonous species such as wheat, barley, rye, rice, or maize. More preferably the plant is of the family Solanaceae. More preferably the plant is of the subfamily Cestroideae. More preferably the plant is one or more of tomato, potato, aubergine, *Petunia* or tobacco. More preferably the plant is of the genus *Nicotiana*. Most preferably the plant is *Nicotiana tabacum*.

The present invention even further provides a plant cell from a plant produced according to the method of the present invention, the plant cell having an altered metabolism. The plant cell produced according to the method of the present invention may have a metabolism which is altered to enhance its metabolism. Preferably, the plant cell produced according to the present invention has a disrupted metabolism.

The present invention also provides a genetically-engineered plant cell comprising a nucleic acid sequence according to the present invention. Preferably the nucleic acid according to the present invention and/or the promoter sequence according to the present invention is operably associated with a coding sequence of a gene.

In an even further aspect of the present invention there is provided a plant cell comprising a recombinant DNA according to the present invention. Preferably the nucleic acid according to the present invention and/or the promoter sequence according to the present invention is operably associated with a coding sequence of a gene.

The present invention also provides a method of regulating the expression of a gene in a plant, the method comprising introducing into the plant a nucleic acid according to the present invention and/or a promoter sequence according to the present invention operably associated with a coding sequence of a gene the expression of which gene is to be regulated.

The present invention further provides a method of modifying the metabolism within a cell of a transgenic plant, the method comprising introducing into a plant a nucleic acid according to the present invention and/or a promoter sequence according to the present invention and/or a chimaeric gene according to the present invention. Preferably the method comprises introducing a nucleic acid according to the present invention and/or a promoter sequence according to the present invention and/or a chimaeric gene according to the present invention into the cell. Preferably the nucleic acid or the promoter sequence according to the present invention is operably associated with a coding sequence of a gene. Advantageously the gene is involved in a metabolic pathway. Preferably a metabolic product is increased or decreased in the cell.

The present invention even further provides a method of altering production of a gene product within a plant cell comprising introducing a nucleic acid according to the present invention and/or a promoter sequence according to the present invention operably associated with a coding sequence of a gene, the production of the gene product of which gene is to be altered. Preferably production of the gene product is increased. Preferably the gene product is an RNA molecule which can interact with the gene expression process via the mechanism of RNAi, antisense, or cosuppression, or which can be translated into a protein gene product. Preferably the protein gene product is a protease, restriction endonuclease, membrane transport protein, ribonuclease or ribosome-inactivating protein. Preferably the ribosome-inactivating protein is pokeweed antiviral protein (PAP). The PAP may be PAP' or PAPII. More preferably the pokeweed antiviral protein is PAP-S or a variant or functional part thereof.

Further provided by the present invention is the use of a nucleic acid comprising a promoter sequence as shown in SEQ ID No.1 or SEQ ID No. 7, or functional part thereof, or a sequence having at least 60% identity thereto for regulating expression of a gene in a plant.

Also provided by the present invention is the use of a nucleic acid sequence comprising the promoter sequence shown in SEQ ID No. 1 or functional part thereof or a sequence having at least 75%, preferably at least 80%, preferably at least 90%, preferably at least 97%, identity thereto, for regulating the expression of a gene in a plant.

Also provided by the present invention is the use of a nucleic acid sequence comprising the promoter sequence shown in SEQ ID No. 7 or functional part thereof or a sequence having at least 75%, preferably at least 80%, preferably at least 90%, preferably at least 97%, identity thereto, for regulating the expression of a gene in a plant.

Also provided by the present invention is the use of a nucleic acid comprising a promoter sequence as shown in SEQ ID No.1 or SEQ ID No.7 or SEQ ID No.4, or functional part thereof, or a sequence having at least 60% identity thereto for altering metabolism within a plant cell.

Also provided by the present invention is the use of a nucleic acid sequence comprising a promoter sequence as shown in SEQ ID No. 1 or functional part thereof or a sequence which is at least 75%, preferably at least 80%, preferably at least 90%, preferably at least 97%, identical thereto for altering metabolism within a plant cell.

Also provided by the present invention is the use of a nucleic acid sequence comprising a promoter sequence as shown in SEQ ID No. 7 or functional part thereof or a sequence which is at least 75%, preferably at least 80%, preferably at least 90%, preferably at least 97%, identical thereto for altering metabolism within a plant cell.

The present invention even further provides the use of a nucleic acid comprising a promoter sequence as shown in SEQ ID No.1 or SEQ ID No. 7 or SEQ ID No.4, or functional part thereof, or a sequence having at least 60% identity thereto for altering production of a gene product within a plant cell.

Also provided by the present invention is the use of a nucleic acid sequence comprising a promoter sequence shown as SEQ ID No. 1 or functional part thereof or a sequence which is at least 75%, preferably at least 80%, preferably at least 90%, preferably at least 97%, identical thereto for altering production of a gene product within a plant cell.

Also provided by the present invention is the use of a nucleic acid sequence comprising a promoter sequence shown as SEQ ID No. 7 or functional part thereof or a sequence which is at least 75%, preferably at least 80%, preferably at least 90%, preferably at least 97%, identical thereto for altering production of a gene product within a plant cell.

The present invention also provides an oligonucleotide probe which selectively hybridizes to a nucleic acid sequence according to the present invention.

The present invention may also provide a part of SEQ ID No. 1, wherein the part is from nucleotide 1 to nucleotide 1321 of SEQ ID No.1 or a part thereof. The part from nucleotide 1 to nucleotide 1321 may be a "functional part" of SEQ ID No. 1.

The present invention may also provide a part of SEQ ID No. 7, wherein the part is from nucleotide 1 to nucleotide 1309 of SEQ ID No. 7 or a part thereof. The part from nucleotide 1 to nucleotide 1309 may be a "functional part" of SEQ ID No. 7.

By "functional part" we mean the part is operable to direct expression in specific cells of a plant.

Any aspect of the present invention may relate to only one, or more than one, of the sequences referred to herein.

The term "chimaeric gene" as used herein means any hybrid nucleic acid molecule formed when nucleic acid sequences from different sources are ligated together. In the present invention "nearby cells" are those cells that are sufficiently close to the specific cells that they are affected by expression in the specific cells, i.e. "nearby cells" may be defined as cells which may differentiate into lateral bud tissue (i.e. once lateral bud initiation cells have been altered in accordance with the present invention), or cells which support the growth of the lateral bud and/or lateral shoot.

SEQUENCE IDENTIFIERS

In the sequence listing:
SEQ ID No. 1 shows the DNA sequence of an isolated promoter of the present invention.
SEQ ID No. 2 shows the PCR Oligonucleotide S2PCLOFWD.
SEQ ID No. 3 shows the PCR Oligonucleotide S2PCLOREV.
SEQ ID No.4 shows the DNA sequence of a further isolated promoter of the present invention (known herein as the "ATC 023 promoter").
SEQ ID No. 5 shows the PCR Oligonucleotide AT4G29190L.
SEQ ID No. 6 shows the PCR Oligonucleotide AT4G29190R.
SEQ ID No. 7 show the DNA sequence of an isolated promoter of the present invention (known herein as the "ATC 085 promoter").
SEQ ID No. 8 shows the Sar8.2b promoter (Genbank accession U64816).

SEQ ID No. 9 shows a region of *Arabidopsis thaliana* genome around the locus AT4g29190 [Chromosome 4: 14396379-14392944 reverse orientation].

BRIEF DESCRIPTION OF THE DRAWINGS

In order that the invention may be readily carried into effect reference will now be made, by way of example, to the following drawings in which;

FIG. 1A through 1E show the alignment of SEQ ID No. 1 with SEQ ID No.8, the Sar8.2b promoter (Genbank accession U648116).

FIG. 2A through 2G show the alignment of SEQ ID No. 4, the ATC 023 promoter sequence, with SEQ ID No. 9, the *Arabidopsis thaliana* genome, around the locus AT4g29190 [Chromosome 4: 14396379-14392944 reverse orientation]. The 5' upstream region of the AT4g29190 gene is shown in italics, and the 5' and 3' untranslated regions are shown in lowercase lettering. Boxes indicate the initiation and termination codons of the AT4g29190 gene. The primer sites used for cloning the ATC 023 promoter are underlined. Nucleotide changes are shown double underlined.

DETAILED DESCRIPTION OF THE INVENTION

Figure 3:
FIG. 3 shows the location of expression of the GUS reporter gene driven by the ATC 085 promoter in tobacco stem sections. (a)-(c) show sections through stem at the region of lateral bud initiation; (d) shows three serial sections through the same lateral bud initiation region; and (e) shows a vertical section through a leaf axil.
Figure 3:
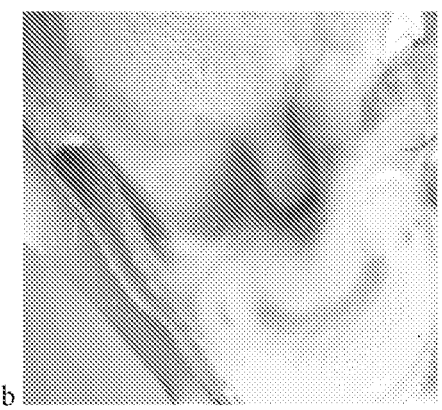
Figure 3:
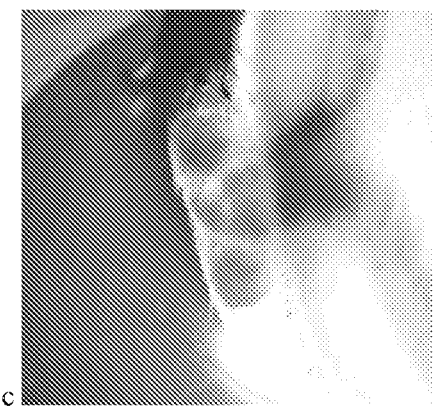
Figure 3:
Figure 3:

Suitably, the promoter sequence according to the present invention comprises a nucleotide sequence which has at least 65%, preferably at least 70%, more preferably at least 75%, more preferably at least 80%, more preferably at least 85%, more preferably at least 90%, more preferably at least 95%, more preferably at least 97% identity, more preferably at least 98% identity, most preferably at least 99% identity with any one of the sequences shown as SEQ ID No. 1 or SEQ ID No. 7 or a functional part thereof.

The term "promoter" as used herein is used in the normal sense of the art, e.g. an RNA polymerase binding site.

As used herein, "altering the metabolism" of a cell means affecting the metabolic function of a cell in such a way as to change the normal functioning metabolism of the cell, resulting in either enhanced or inhibited normal function of the cell.

As used herein, the term "disrupting the metabolism" means altering the metabolic function of a cell in such a way as to interfere with the normal functioning metabolism of the cell, resulting in the death or inhibition of the normal function of the cell.

As used herein, the term "enhancing the metabolism" of a cell means altering the metabolic function of a cell in such a way as to increase the growth or viability of the cell.

As used herein, "lateral bud initiation cell" means a cell associated with the initiation of the growth of a lateral bud.

As used herein, "modifying morphology" means altering the normal growth habit of a plant which manifests as a physical change to part or all of the plant. The growth of the lateral shoots of the plant may be enhanced, for example. Preferably the growth of the lateral shoots of the plant is inhibited or prevented. Either way the overall physical structure and/or appearance of the plant may be changed.

A plant DNA sequence may be recovered from the cells of the natural host, or it may be synthesized directly in vitro. Extraction from the natural host enables the isolation de novo of novel sequences, whereas in vitro DNA synthesis generally requires pre-existing sequence information. Direct chemical in vitro synthesis can be achieved by sequential manual synthesis or by automated procedures. DNA sequences may also be constructed by standard techniques of annealing and ligating fragments, or by other methods known in the art. Examples of such cloning procedures are given in Sambrook et al. (1989).

The DNA sequence of the present invention may be isolated by direct cloning of segments of plant genomic DNA. Suitable segments of genomic DNA may be obtained by fragmentation using restriction endonucleases, sonication, physical shearing, or other methods known in the art. By using predictive screening of the DNA sequence of the cloned segment for the presence of coding sequences (Baxevanis, 2001) motifs characteristic of known promoter sequences may be found upstream of such a diagnostic sequence.

The identification of the cloned segment as a promoter sequence may alternatively be achieved by assessing functionality, for example by linking the cloned segment with a coding sequence derived from a reporter gene and introducing the chimaeric construct into a host cell or cell-free system wherein expression of the reporter gene can be evaluated. This process may form part of another sequence isolation strategy termed promoter trapping, wherein genomic DNA fragments are cloned directly into "expression vectors" comprising a reporter gene coding region and other sequences necessary for expression in a host cell or cell-free system. The expression may or may not require integration of the chimaeric construct into the host's chromosomal DNA.

An alternative method of obtaining a DNA sequence of the present invention is by the identification and isolation of a DNA coding sequence which is known to be expressed and subsequently using this sequence to obtain the contiguous promoter sequence, which is by definition directing the expression of the coding sequence. Alternatively a DNA sequence may be obtained by identification of a sequence which is known to be expressed in a different organism, and then isolating the homologous coding sequence and subsequently its associated promoter sequence from the organism of choice. A coding sequence may be obtained by the isolation of messenger RNA (mRNA or polyA+RNA) from plant tissue or isolation of a protein and performing "back-translation" of its sequence. The tissue used for RNA isolation is selected on the basis that suitable gene coding sequences are believed to be expressed in that tissue at optimal levels for isolation.

Various methods for isolating mRNA from plant tissue are well known to those skilled in the art, including for example using an oligo-dT oligonucleotide immobilised on an inert matrix. The isolated mRNA may be used to produce its complementary DNA sequence (cDNA) by use of the enzyme reverse transcriptase (RT) or other enzymes having reverse transcriptase activity. Isolation of an individual cDNA sequence from a pool of cDNAs may be achieved by cloning into bacterial or viral vectors, or by employing the polymerase chain reaction (PCR) with selected oligonucleotide primers. The production and isolation of a specific cDNA from mRNA may be achieved by a combination of the reverse transcription and PCR steps in a process known as RT-PCR.

Various methods may be employed to improve the efficiency of isolation of the desired sequence through enrichment or selection methods including the isolation and comparison of mRNA (or the resulting single or double-stranded cDNA) from more than one source in order to identify those sequences expressed predominantly in the tissue of choice. Numerous methods of differential screening, hybridisation, or cloning are known to those skilled in the art including cDNA-AFLP, cascade hybridisation, and commercial kits for selective or differential cloning.

In the present invention, a cDNA sequence to a SAR 8.2j protein (EMBL Accession Number U64812) was utilised to isolate a novel promoter sequence. Examples of other SAR protein genes are given in EMBL Accession Nos. U64816, U64807, U64808, U64809, U64810, U64811, U64813, U64814, U6481. A second cDNA sequence to a Zinc Finger Transcription Factor (EMBL Accession Number AL096692) was also utilised to isolate a promoter sequence.

The selected cDNA may then be used to evaluate the genomic features of its gene of origin, by use as a hybridisation probe in a Southern blot of plant genomic DNA to reveal the complexity of the genome with respect to that sequence. Alternatively, sequence information from the cDNA may be used to devise oligonucleotides and these can be used in the same way as hybridisation probes; for PCR primers to produce hybridisation probes, or for PCR primers to be used in direct genome analysis.

Similarly the selected cDNA may be used to evaluate the expression profile of its gene of origin, by use as a hybridisation probe in a Northern blot of RNA extracted from various plant tissues, or from a developmental or temporal series. Again sequence information from the cDNA may be used to devise oligonucleotides which can be used as hybridisation probes, to produce hybridisation probes, or directly for RT-PCR.

The selected cDNA, or derived oligonucleotides, may then be used as a hybridisation probe to challenge a library of cloned genomic DNA fragments and identify overlapping DNA sequences. By this means a contiguous promoter may be identified and isolated.

By the nature of the method of isolation, an isolated cDNA usually comprises the 3' terminus of the coding region and extends towards the 5' terminus. It may not comprise the full-length coding sequence. It is preferable to ensure that the 5' terminal sequence is present if the cDNA is to be used to identify the contiguous promoter. This may be achieved by extension of the cloned cDNA sequence in the 5' direction by a process termed 5' RACE (rapid amplification of cDNA ends).

If sequence analysis of the cloned cDNA identifies a homologous sequence already reported in the scientific literature, this information may provide a suitable candidate sequence for the 5' terminus. However, the possibility of there being different members of the same gene family with similar coding regions, but differing intron regions, promoter sequences and expression profiles, may lead to the selection of an incorrect and unsuitable promoter sequence.

Once the 5' terminus of the coding sequence has been identified, the contiguous upstream region containing the promoter may be identified if present in the public Nucleotide databases. Alternatively the promoter may be isolated, by further extension in the 5' direction. This may be achieved by methods including vector-ligation PCR, genome walking, vectorette PCR, and other methods. If necessary the process may be repeated with a new primer complementary to the 5' terminus of the first promoter fragment to ensure that all the control sequences of the promoters are isolated.

The present invention also provides for the use of a DNA sequence as shown in SEQ. ID. No: 4, the sequence encoding a promoter (and referred to herein as "ATC 023"), the sequence being able to control the expression of a Zinc finger transcription factor protein, and which may be used as a plant promoter. This sequence is identified on the TAIR Nucleotide Sequence database at Locus AT4g29190. The present invention also includes DNA sequences which control the expression of other Zinc finger transcription factor protein genes and which have some regions of homology with the DNA sequence of SEQ. ID. No: 4.

Homology may be determined on the basis of percentage identity between two DNA (or polypeptide) sequences. In general the two sequences to be compared are aligned to give a maximum correlation between the sequences. The alignment of the two sequences is examined and the number of positions giving an exact nucleotide (or amino acid) correspondence between the two sequences determined, divided by the total length of the alignment multiplied by 100 to give a percentage identity figure. This percentage identity figure may be determined over the whole length of the sequences to be compared, which is particularly suitable for sequences of the same or very similar lengths and which are highly homologous, or over shorter defined lengths, which is more suitable for sequences of unequal length or which have a lower level of homology.

Methods for comparing the identity of two or more sequences are well known in the art. Thus for instance, programs available in the Wisconsin Sequence Analysis Package, version 9.1 (Devereux J. et al, 1984) (available from Genetics Computer Group, Madison, Wis., USA), for example the programs BESTFIT and GAP, may be used to determine the percentage identity between two polynucleotides and the percentage identity between two polypeptide sequences. BESTFIT uses the "local homology" algorithm of Smith and Waterman (1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Needleman and Wunsch (1970). GAP is more suited to comparing sequences which are approximately the same length and an alignment is expected over the entire length. Preferably the parameters "Gap Weight" and "Length Weight" used in each program are 50 and 3 for polynucleotide sequences and 12 and 4 for polypeptide sequences, respectively. Preferably, percentage identities and similarities are determined when the two sequences being compared are optimally aligned.

Other programs for determining identity and/or similarity between sequences are also known in the art, for instance the BLAST family of programs (Karlin & Altschul, 1990, *Proc. Natl. Acad. Sci. USA* 87:2264-2268, modified as in Karlin & Altschul, 1993, *Proc. Natl. Acad. Sci. USA* 90:5873-5877, available from the National Center for Biotechnology Information (NCBI), Bethesda, Md., USA and accessible through the home page of the NCBI at www.ncbi.nlm.nih.gov). These programs exemplify a preferred, non-limiting example of a mathematical algorithm utilized for the comparison of two sequences. Such an algorithm is incorporated into the NBLAST and XBLAST programs of Altschul, et al., 1997, *J. Mol. Biol.* 215:403-410. BLAST nucleotide searches can be performed with the NBLAST program to obtain nucleotide sequences homologous to a nucleic acid molecule of the invention. BLAST protein searches can be performed with the XBLAST program, to obtain amino acid sequences homologous to a protein molecule of the invention. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov. Another preferred non-limiting example of a mathematical algorithm utilized for the comparison of sequences is the algorithm of Myers and Miller, 1988, *CABIOS* 4:11-17. Such an algorithm is incorporated into the ALIGN program (version 2.0) which is part of the GCG sequence alignment software package.

Another non-limiting example of a program for determining identity and/or similarity between sequences known in the art is FASTA (Pearson W. R. and Lipman D. J., Proc. Nat. Acac. Sci., USA, 85:2444-2448, 1988, available as part of the Wisconsin Sequence Analysis Package). Preferably the BLOSUM62 amino acid substitution matrix (Henikoff S. and Henikoff J. G., Proc. Nat. Acad. Sci., USA, 89:10915-10919, 1992) is used in polypeptide sequence comparisons including where nucleotide sequences are first translated into amino acid sequences before comparison.

The percent identity between two sequences can be determined using techniques similar to those described above, with or without allowing gaps. In calculating percent identity, typically exact matches are counted.

Preferably the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

In the context of the present invention substantially homologous sequences are those which have at least 50% sequence identity, preferably at least 60%, 65% or 70% sequence identity, more preferably at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94% sequence identity and most preferably at least 95%, 96%, 97%, 98% or 99% or above sequence identity.

As used herein, the term "homologue" means an entity having a certain homology with the subject amino acid sequences and the subject nucleotide sequences. Here, the term "homology" can be equated with "identity".

Although homology can also be considered in terms of similarity (i.e. amino acid residues having similar chemical properties/functions), in the context of the present invention it is preferred to express homology in terms of sequence identity.

In the context of the present invention the term utilising includes, amongst others, using, introducing and expressing a sequence or gene.

The present invention also includes DNA sequences which hybridize to the DNA sequences of the above promoters, including partial sequences and complementary sequences. Conditions under which such sequences will so hybridize can be determined in a routine manner.

Hybridization can be performed under low, medium or high stringency conditions. The conditions under which hybridization and/or washing can be carried out can range from 42° C. to 68° C. and the washing buffer can comprise from 0.1×SSC, 0.5% SDS to 6×SSC, 0.5% SDS. Typically, hybridization can be carried out overnight at 65° C. (high stringency conditions), 60° C. (medium stringency conditions), or 55° C. (low stringency conditions). The filters can be washed for 2×15 minutes with 0.1×SSC, 0.5% SDS at 65° C. (high stringency washing). The filters may be washed for 2×15 minutes with 0.1×SSC, 0.5% SDS at 63° C. (medium stringency washing). For low stringency washing, the filters are washed at 60° C. for 2×15 minutes at 2×SSC, 0.5% SDS.

The present invention also includes DNA sequences which hybridize to oligonucleotide probes. Preferably the DNA sequences hybridize to oligonucleotide probes under stringent conditions. In instances wherein the nucleic acid molecules are oligonucleotides ("oligos"), highly stringent conditions may refer, for example, to washing in 6×SSC/ 0.05% sodium pyrophosphate at 37° C. (for 14 base oligos), 48° C. (for 17 base oligos), 55° C. (for 20 base oligos), and 60° C. (for 23 base oligos). In a BLAST search against the EMBL Nucleotide Sequence Database, release 77 (Kulikova et al, 2004), the ATC 085 promoter has a greater than 90% identity over its last 220 bases with known sequences upstream of the translation start codon of other SAR genes such as 8.2h and 8.2k. The only sequence showing any other regions of homology along the length of the promoter is the Sar 8.2b promoter region (SAR 8.2b promoter, Genbank accession U64816, bases 1 to 1907).

FIG. 1A through 1E show the alignment between SEQ ID No. 1 (bases 1 to 1566) and the region of the SAR 8.2b promoter with homology (bases 704 to 1907 of the Genbank sequence). Identity is shown by dots between the aligned sequences. From FIG. 1A through 1E, it can be seen that SEQ ID No. 1 has a 61% identity with the corresponding SAR 8.2b promoter overall.

FIG. 2A through 2G show the alignment between the sequence of the ATC 023 promoter (bases 1 to 1904) and the region of the *Arabidopsis thaliana* sequence around the locus AT4g29190 (in reverse orientation). From FIG. 2A through 2G, it can be seen that the ATC 023 promoter as cloned has over 99% identity with the reported genomic sequence.

The gene coding sequence that is used under the control of the promoter and employed in carrying out the present invention may be active in some or all plant tissues. The sequence employed may encode a protein or an RNA moiety. Through recombinant DNA techniques the sequence may encode a synthetic variant of a protein or RNA, a partial sequence, or a composite sequence comprising regions from one or more genes. For example, the chimaeric gene may encode a polyprotein. The sequence may also comprise repeated, truncated, inverted or complementary sequences, to achieve disruption of the transcription and translation of an endogenous gene or genes by, for example, antisense, cosuppression, or RNA inhibition technology.

Many plant, bacterial and viral genes may be actively expressed under the control of the promoter. Preferably such genes encode:

(i) GUS, GFP and luciferase enzymes which may be used as reporter genes for promoter function.

(ii) Genes for enzymes producing structural components of the plant such as cellulose, hemicelluloses, pectins and lignin.

(iii) DNA sequences designed to alter the metabolism in plants and plant cells. Such genes include those for carbohydrate metabolism, starch metabolism, amino acid and protein metabolism, nucleic acid metabolism and lipid metabolism.

(iv) Regulatory DNA sequences which may have effects on the control of metabolism or development, such as flowering or plant architecture, including those genes involved in the metabolism or transport of plant growth substances.

(v) DNA sequences encoding products such as restriction enzymes, proteases, proteinase inhibitors and ribosome inactivating proteins which can be used to deliberately impair cell function.

(vi) Resistance to environmental stress, or to pathogens or to pests.

The promoter of the present invention is preferably operable to direct expression in lateral and/or auxiliary meristems.

The promoter according to the present invention may in addition to being operable to direct expression in lateral buds and/or shoots, be operable to direct expression in other tissues and/or cells of the plant. For instance, some expression may be observed in wound tissue, and/or the stem and/or the leaves of the plant. However, the promoter is operable to direct expression substantially specifically (as defined herein) in a lateral bud and/or lateral shoot.

The expression profile of the promoters of the present invention may be determined by those skilled in the art using a variety of methods which are preferably:

(i) Transient expression where the promoter is linked to a reporter gene such as GUS, GFP or luciferase in an appropriate construct and introduced into plant tissue by shotgun transformation. Promoter expression is detected by the presence or absence of the reporter gene product in different plant tissues.

(ii) Transient expression where the promoter is linked to a reporter gene such as GUS, GFP or luciferase in an appropriate binary construct and introduced into plant tissue by *Agrobacterium*. Promoter expression is detected by the presence or absence of the reporter gene product in different plant tissues. The GUS activity can be detected visually using appropriate substrates as a stain, or by using a colorimeter or spectrophotometer; luciferase and fluorescent marker proteins can be detected by eye or photographically, either on film or digital medium, or quantitatively using a luminometer or fluorometer. Marker genes may also be detected using antibody based systems.

(iii) Plant transformation and regeneration. Promoter expression is detected by the presence or absence of the reporter gene in different plant tissues.

(iv) Plant transformation and regeneration. Promoter expression is detected by the presence or absence of a specific gene product produced by an effector gene in different plant tissues.

The gene product of the present invention may be produced by recombinant techniques, wherein genomic DNA clones or cDNA clones for the DNA coding sequence are produced, isolated, proliferated, and incorporated into a plant transformation vector of the present invention.

The present application is the first time that a promoter which is capable of expressing a gene substantially specifically in lateral bud and/or lateral shoots has been presented.

Suitably, the promoter according to the present invention is an "induced promoter", i.e. one which is switched on in response to a stimulus. Thus, as well as the promoter being operable to direct expression in specific cells of the plant, the promoter may also be considered as an inducible promoter.

Preferably, the promoter according to the present invention is induced by topping the plant, i.e. removing the apical bud or shoot of the plant.

Without wishing to be bound by theory, one possible manner in which the promoter of the present invention may be "switched on" is that it may be activated or induced by a signal which may be stimulated by the removal of the apical bud, thus after topping. For instance, the signal may be a plant growth hormone. By way of example only the signal may be a cytokinin(s).

Alternatively, again without being bound by theory, it may be possible that the apical bud releases an inhibitory signal which prevents lateral meristem outgrowth and/or the switching on the promoter of the present invention. In which case, for example, the removal of the apical bud, e.g by topping, may result in the loss of the inhibitory signal and thus the switching on of the promoter of the present invention. For instance, by way of exampley only, the inhibitory signal may be a auxin(s).

Isolated

In one aspect, preferably the sequence is in an isolated form. The term "isolated" means that the sequence is at least substantially free from at least one other component with which the sequence is naturally associated in nature and as found in nature.

Purified

In one aspect, preferably the sequence is in a purified form. The term "purified" means that the sequence is in a relatively pure state—e.g. at least about 90% pure, or at least about 95% pure or at least about 98% pure.

Nucleotide Sequence

The term "nucleotide sequence" as used herein is synonymous with "nucleic acid sequence" and refers to an oligonucleotide sequence or polynucleotide sequence, and variants, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" or "nucleic acid" in relation to the present invention includes genomic DNA, cDNA, synthetic DNA, and RNA. Preferably it means DNA, more preferably cDNA sequence coding for the present invention.

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence however, the amended nucleotide sequence would encode for the same, or a variant, primary amino acid sequence as the original nucleotide sequence.

Therefore, the present invention further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once a promoter-encoding nucleotide sequence has been isolated, or a putative promoter-encoding nucleotide sequence has been identified, it may be desirable to modify the selected nucleotide sequence, for example it may be desirable to mutate the sequence in order to prepare an gene product in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. Suitable methods for performing 'shuffling' can be found in EP0 752 008, EP1 138 763, EP1 103 606.

Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known proteins. Such variants thereby obtained may have significant structural analogy to known proteins, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

Plant Transformation Vectors

Plant transformation vectors of the present invention will contain "expression cassettes" comprising 5'-3' in the direction of transcription, a promoter sequence as described in the present invention, a gene coding sequence as discussed above and, optionally a 3' untranslated, terminator sequence including a stop signal for RNA polymerase and a polyadenylation signal for polyadenylase.

The promoter sequence may be present in one or more copies, and such copies may be identical or variants of the promoter sequence as described above. Such copies may also be complete or partial sequences as described above.

The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The expression cassette may also comprise a gene expression enhancing mechanism to increase the strength of the promoter. An example of such an enhancer element is that derived from a portion of the promoter of the pea plastocyanin gene, and which is the subject of International Patent Application No. WO 97/20056.

These regulatory regions may be derived from the same gene as the promoter DNA sequence of the present invention or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The gene coding sequence may be derived from the same gene as the promoter DNA sequence of the present invention or may be derived from a different gene, from *Nicotiana tabacum*, or another organism, for example from a plant of the family Solanaceae, or from the subfamily Cestroideae.

The expression cassette may be incorporated into a basic plant transformation vector, such as pBIN 19 Plus, pBI 101, or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "plant transformation vector" means a construct capable of in vivo or in vitro expression.

Preferably, the expression vector is incorporated in the genome of the organism. The term "incorporated" preferably covers stable incorporation into the genome.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced. The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

The term "operably associated" refers to a juxtaposition wherein the components described are in a relationship permitting them to function in their intended manner. A regulatory sequence "operably associated" to a coding sequence is ligated in such a way that expression of the coding sequence is achieved under conditions compatible with the control sequences.

Host Cells

The term "host cell"—in relation to the present invention includes any cell that comprises a nucleic acid, a promoter sequence or a chimaeric gene according to the present invention or an expression vector as described above.

Thus, a further embodiment of the present invention provides host cells transformed or transfected with a nucleic acid, a promoter sequence or a chimaeric gene of the present invention. The cells will be chosen to be compatible with the said vector and may for example be prokaryotic (for example bacterial), fungal, yeast or plant cells. Preferably, the host cells are not human cells.

Examples of suitable bacterial host organisms are gram negative bacteria or gram positive bacteria.

In one embodiment, eukaryotic hosts such as yeasts or other fungi may be preferred. In general, yeast cells are preferred over fungal cells because they are easier to manipulate.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

The term "transgenic plant" in relation to the present invention includes any plant that comprises a nucleic acid, a promoter sequence or a chimaeric gene of the present invention. Preferably the nucleic acid, promoter sequence or chimaeric gene is incorporated in the genome of the plant.

The term "transgenic plant" does not cover native nucleotide coding sequences in their natural environment when they are under the control of their native promoter which is also in its natural environment.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

The term "variant" as used herein means a protein expressed from a non-endogenous genetic code resulting in one or more amino acid alterations (i.e. amino acid deletions, additions or substitutions) when compared with the natural or wild-type sequence within the mature protein sequence.

Plant Transformation

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Typically, in *Agrobacterium*-mediated transformation a binary vector carrying a foreign DNA of interest, i.e. a chimaeric gene, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998) whereby floral buds of an intact plant are brought into contact with a suspension of the *Agrobacterium* strain containing the chimeric gene, and following seed set, transformed individuals are germinated and identified by growth on selective media.

Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208.

Further suitable transformation methods include direct gene transfer into protoplasts using polyethylene glycol or electroporation techniques, particle bombardment, microinjection and the use of silicon carbide fibres for example.

Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994). Production of fertile transgenic maize plants by silicon carbide whisker-mediated transformation is taught in *The Plant Journal* 6: 941-948) and viral transformation techniques is taught in for example Meyer P, Heidmann I & Niedenhof I (1992). The use of cassava mosaic virus as a vector system for plants is taught in *Gene* 110: 213-217.

Further teachings on plant transformation may be found in EP-A-0449375.

In a further aspect, the present invention relates to a vector system which carries a nucleotide sequence or construct according to the present invention and which is capable of introducing the nucleotide sequence or construct into the genome of an organism, such as a plant. The vector system may comprise one vector, but it may comprise two vectors. In the case of two vectors, the vector system is normally referred to as a binary vector system. Binary vector systems are described in further detail in Gynheung An et al., (1980), Binary Vectors, *Plant Molecular Biology Manual* A3, 1-19.

One extensively employed system for transformation of plant cells uses the Ti plasmid from *Agrobacterium tumefaciens* or a Ri plasmid from *Agrobacterium rhizogenes* An et al., (1986), *Plant Physiol*. 81, 301-305 and Butcher D. N. et al., (1980), *Tissue Culture Methods for Plant Pathologists*, eds.: D. S. Ingrams and J. P. Helgeson, 203-208. After each introduction method of the desired promoter or construct or nucleotide sequence according to the present invention in the plants, the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., *Crit. Rev. Plant Sci.*, 4:1-46; and An et al., *EMBO J.* (1985) 4:277-284.

Plant cells may be grown and maintained in accordance with well-known tissue culturing methods such as by culturing the cells in a suitable culture medium supplied with the necessary growth factors such as amino acids, plant hormones, vitamins, etc.

Culturing and Production

Host cells transformed with the nucleic acid, promoter sequence or chimaeric gene of the present invention may be cultured under conditions conducive to the growth of the host.

The medium used to cultivate the cells may be any conventional medium suitable for growing the host cell in questions.

Production of the Gene Product

Expression of a DNA coding sequence or nucleic acid sequence in the plant host cell will produce an RNA transcript. This transcript may be a RNA molecule which is not subsequently translated into a protein product, but which may interact with the gene expression process via the mechanism of RNAi, antisense, or cosuppression. If the coding sequence is derived from a structural gene, the RNA transcript may then be translated into a protein gene product. If desired, the gene product can be isolated by standard techniques for isolating proteins from biological systems, such as salt precipitation, column chromatography, immunoaffinity techniques, electrophoresis, recrystallisation, centrifugation, and such like.

Expression of a Gene Product Detrimental to Plant Cells

If the DNA coding sequence or nucleic acid sequence is translated into a protein gene product which has a detrimental effect on the plant host cell, this can be used in a plant cell death system, by using the promoter of the present invention promoter to direct expression in particular plant cells. Suitable proteins having a detrimental effect could include proteases, restriction endonucleases, membrane transport proteins, and ribonucleases such as Barnase. Other examples include ribosome-inactivating proteins (RIPs) such as the maize RIP b-32 protein, ricin, abrin, modeccin, barley translation inhibitor and pokeweed antiviral protein (PAP). Pokeweed (*Phytolacca americana*) produces three distinct antiviral proteins, namely PAP', PAPII and PAP-S. International Patent Publication No. WO02/33107 demonstrates the use of truncated variants of the PAP-S protein in a cell death system. Hence, the use of a Ribosome Inactivating Protein (RIP) such as Pokeweed Antiviral Protein (PAP) or variants thereof would provide a plant cell death system.

The invention will now be described, by way of example only, with reference to the following Examples.

EXAMPLE 1

Isolation of the ATC 085 Promoter (SEQ ID No. 7) Region, and Production of Transformation Constructs Genomic DNA of tobacco leaf tissue was isolated using the DNAeasy Plant Miniprep Kit (Qiagen) according to the manufacturers' instructions from K326 tobacco leaf material. A 1 µL aliquot of a 1:10 diluted preparation of genomic DNA was used for a primary PCR using 1 µL of a PCR primer S2PCLOFWD (SEQ ID No. 2) at 10 pM/µL and 1 µL of a PCR primer S2PCLOREV (SEQ ID No. 3) at 10 pM/µL in a 25 µL reaction containing 0.5 µL Elongase Taq DNA Polymerase (Gibco BRL), 1 µL Elongase buffer A, 4 µL Elongase buffer B, 1 µL dNTPs at 5 mM each, 15.5 µL double distilled water. The PCR reaction conditions were: an initial cycle at 94° C. for 2 minutes followed by 35 cycles of 94° C. for 30 seconds, 60° C. for 30 seconds and 68° C. for 4 minutes, followed by a final cycle of 68° C. for 10 minutes. The PCR reaction was electrophoresed on a 1.2% agarose TBE gel, containing traces of ethidium bromide, at 4V/cm for 2 hours. Two PCR products were seen. The larger product of approximately 1600 bp was excised from the gel and the DNA purified using the QiaQuick gel extraction kit (Qiagen) following the manufacturers' procedures.

The purified PCR product was cloned into TOPO vector (Invitrogen) and transformed into TOP10 Chemically Competent *E. coli* (Invitrogen) following the manufacturers' standard procedure. An aliquot of the reaction was plated onto sterile LB agar containing kanamycin and the plates were incubated overnight at 37° C. Colonies were screened by PCR using the conditions above to identify clones containing the promoter. The sequence was further confirmed by sequencing.

The ATC085 promoter was excised from the TOPO vector as a HindIII-BamHI fragment and cloned into the plant transformation vector pBin 19 Plus vector based on pGPTV-Kan (Becker et al, 1992) derived from pBIN19 (Bevan et al, 1984) in front of three different reporter genes to give the constructs, GUS (ATC vector pBNP085-0040-001), GFP (ATC vector pBNP085-0003-001), and Luciferase (ATC vector pBNP085-0017-001). The promoter was also cloned in front of an effector gene, the active form of the pokeweed antiviral protein S from *Phytolacca americana* (ATC vector pBNP085-0501-001). pBNP085-0501-001 has been deposited by Advanced Technologies (Cambridge) Ltd, 210 Cambridge Science Park, Cambridge CB4 0WA under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 20 Sep. 2005 under accession number NCIMB 41343.

EXAMPLE 2

Isolation of the ATC 023 Promoter Region and Production of Transformation Construct The ATC023 promoter was isolated by PCR from *Arabidopsis thaliana* (Columbia ecotype) genomic DNA using PfuTurbo DNA Polymerase (Stratagene), and the primers AT4G29190L (SEQ. ID. No. 5) and AT4g29190R (SEQ. ID. No. 6) containing restriction sites for HindIII and BamHI respectively, at an annealing temperature of 63° C. The restriction sites were then used to clone the isolated fragment into the plant transformation vector pBI101 in front a GUS reporter gene to give the construct pBI101 023-0101-001. The construct was then transformed into *E. coli* DH5α.

EXAMPLE 3

Production of Transformed Tobacco Plants

The constructs produced above were transferred into the *Agrobacterium tumefaciens* strain LBA4404 and transgenic tobacco var. K326 plants were obtained by in vitro transformation of leaf discs using the co-cultivation method of Horsch et al (1985). Transformed callus and regenerating shoots were selected on MS Agar media containing 100 μg/ml kanamycin and cultured in the presence of Claforan to remove the *Agrobacterium* cells. Plants were then kept and multiplied in vitro on media without Claforan to confirm absence of *Agrobacterium*.

Plants were transferred to soil in the greenhouse for characterisation. The plants showed growth characteristics indistinguishable from the wild type tobacco plant in the greenhouse. PCR analysis was conducted to identify transgenic plants.

For the production of subsequent generations plants can be selfed and seed collected from mature seed heads and stored at 6° C. Segregation ratios in progeny from selfed transgenic plants can be used to select seed batches that contain single insertion sites based on a 3:1 ratio. The number of inserts can also be determined by Southern hybridisation. The insertion into the tobacco genome can be characterised by genome walking.

EXAMPLE 4

Production of Transgenic *Arabidopsis* Plants

The constructs described above were transferred into the *Agrobacterium tumefaciens* strains LBA4404 and GV3103, and used to transform *Arabidopsis thaliana* by the floral dip method of Clough and Bent (1998). After seed collection from dipped plants, T1 transformants were screened using selection on 40 μg/ml kanamycin on ATS/Phytagel™ or 50 μg/ml kanamycin on MS/Agar media. Independent transformants were isolated in this way and these were transferred to soil and grown under long-day conditions.

Plants were allowed to self-pollinate to generate T2 seed. Approximately 60 T2 seed from the independent lines was screened again on kanamycin, and Chi squared tests were used to determine whether the segregation ratio observed was consistent with a single site of transgene insertion (3 resistant:1 sensitive). Multiple independent lines with ratios consistent with a single insertion site were identified, and the remaining lines were discarded.

EXAMPLE 5

Characterisation of the ATC 085 Promoter-GUS Expression in Tobacco Plants

Sixty plants transformed with the vector pBNP085-0040-001 were used for GUS analysis. After approximately 6-8 weeks growth in the greenhouse when the apical bud had reached the "floral button" stage, the plants were either topped using a scalpel at the internode above the 18$^{th}$ leaf (counting from the base), wounded by excising half of the blades of leaves 16, 17 and 18, or left untreated. After 24 hours, various tissue samples were taken, including stem sections at the base of lateral buds 14, 15, 16, 17 and 18, internodal stem sections, apical flowering shoots where present, leaf blades and petioles, and primary and secondary roots. All tissue collected was immediately immersed in 0.1M potassium phosphate buffer pH 7.0 containing 0.1% β-mercaptoethanol to prevent browning.

Staining solution was prepared as follows: 300 mg X-gluc powder was dissolved in 3 ml DMSO in a glass container and made up to 1 L with 0.1M potassium phosphate buffer containing 0.5 mM potassium ferricyanide, 0.5 mM potassium ferrocyanide, 10 mM EDTA, 0.1% Triton-X and 0.067% Sarcosyl. This solution was stored at 4° C. in darkness.

For staining the tissue samples, the potassium phosphate/β-mercaptoethanol buffer was replaced with fresh staining solution ensuring the tissue was fully submerged, and the samples were incubated overnight at 37° C. in the dark. The staining solution was then replaced with 70% ethanol and the tissues were stored in the dark at room temperature until they had cleared. It was sometimes necessary to change the ethanol at least once for leaf material. Once the tissue had cleared, the ethanol was replaced with acidified glycerol. Samples were observed and photographed under a microscope.

GUS expression was detected in the plants after all three treatments (topped, wounded, or untreated) and this was localised at the base of the lateral buds and/or in the stem close to the point of lateral bud initiation in every case (FIG. 3). A large proportion of the plants exhibited expression at every bud position sampled. Expression at the lateral buds was detected irrespective of the pre-treatment (topping, wounding, or untreated). In the large majority of plants, no expression was detected in any other tissues—only in a few anomalous plants were any other sites of expression observed, predominantly at the cut edges of the wounded leaves. Hence the ATC085 promoter was shown to be a promoter directing substantially specific expression at or around the point of lateral bud initiation.

EXAMPLE 6

Characterisation of the ATC 085 Promoter-GFP Expression in Plants

Plants transformed with the vector pBNP085-0003-001 were used for analysis of GFP expression. Whole plants or plant parts, sections of plants or plant tissues were irradiated with blue light and inspected for green fluorescence either by eye or through a microscope.

EXAMPLE 7

Characterisation of ATC 085 Promoter—Luciferase Expression in Plants

Plants transformed with the vector pBNP085-0017-001 were used for analysis of Luciferase expression. Whole plants, parts of plants or sections of plants or plant tissues were moistened or sprayed with 1 mM luciferin (Sigma) and incubated in the dark for 15 minutes. Luciferase expression could then be visualised either by autoradiography onto X-ray film, or by photography using a digital camera with a long exposure time or by using a photon capture device such as an image intensifier linked to a camera system.

EXAMPLE 8

Characterisation of ATC 085 Promoter—PAP Expression in Tobacco Plants

Twenty-one transgenic and five control untransformed (non-co-cultivated or NCC) plants were grown in the greenhouse, and after 6 to 8 weeks, the plants were topped using a scalpel at the internode above the 18$^{th}$ leaf to remove the apical inflorescence and uppermost leaves as described above. The outgrowth of lateral shoots from the axils of the 16th, 17th and 18th leaf was monitored daily for 29 days and scored on the following system of size classes:
0=lateral bud abutting the main stem
1=lateral bud on elongated lateral stem (i.e. 1 internode)
2=lateral shoot with 2 internodes
3=lateral shoot with 3 internodes etc.

Figure 4A:
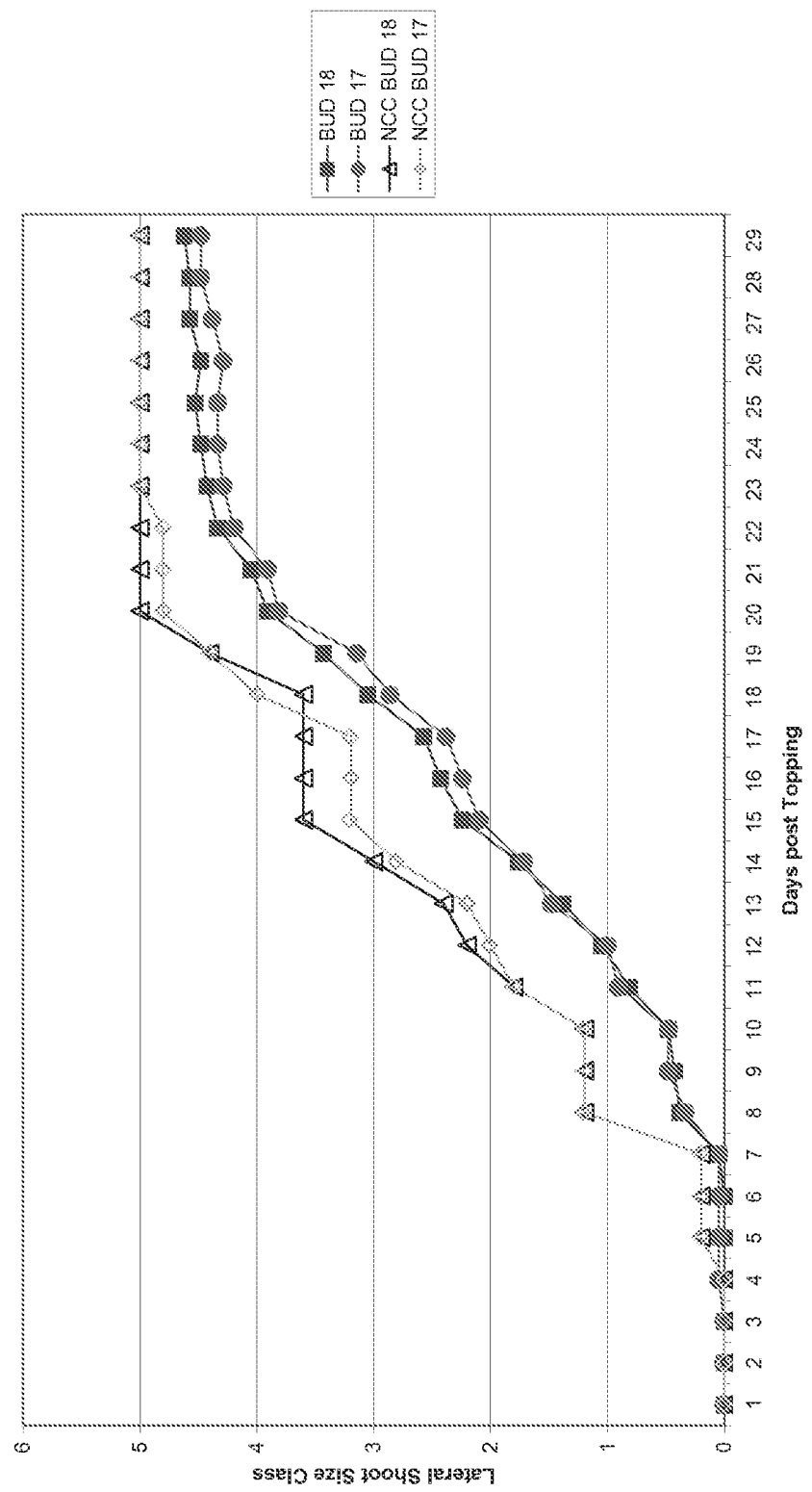
FIG. 4a shows the effect of expression of the Pokeweed antiviral protein driven by the ATC 085 promoter on the outgrowth of lateral buds 17 and 18 in tobacco following topping compared with control (NCC) plants.
Figure 4B:
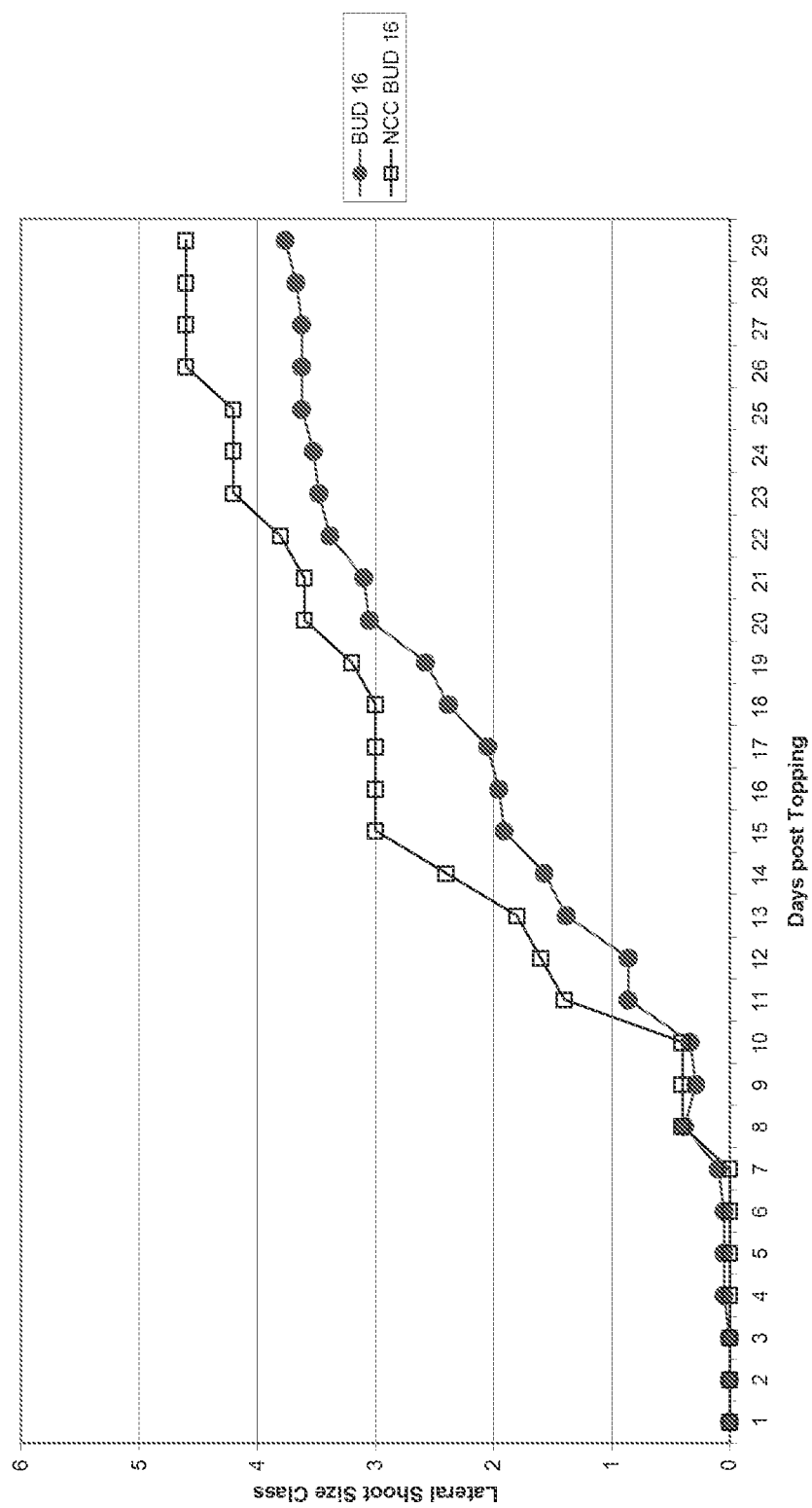
FIG. 4b shows the effect of expression of the Pokeweed antiviral protein driven by the ATC 085 promoter on the outgrowth of lateral bud 16 in tobacco following topping compared with control (NCC) plants.

From these data the mean outgrowth from the three lateral bud positions on each day was calculated for the transgenic and untransformed plants. These data are plotted in FIG. 4. It is clear that the localised expression of the Pokeweed antiviral protein directed by the ATC085 promoter has caused a significant delay in the onset of outgrowth of lateral shoots stimulated upon topping and a reduction in the amount of outgrowth by Day 29 when compared to the control plants. The effect was particularly marked in the two uppermost buds 17 and 18 (see FIG. 4a). Lateral bud 16 showed less outgrowth (FIG. 4b) upon topping than buds 17 and 18, but this was further reduced by expression of the ATC 085-PAP construct.

Figure 5:
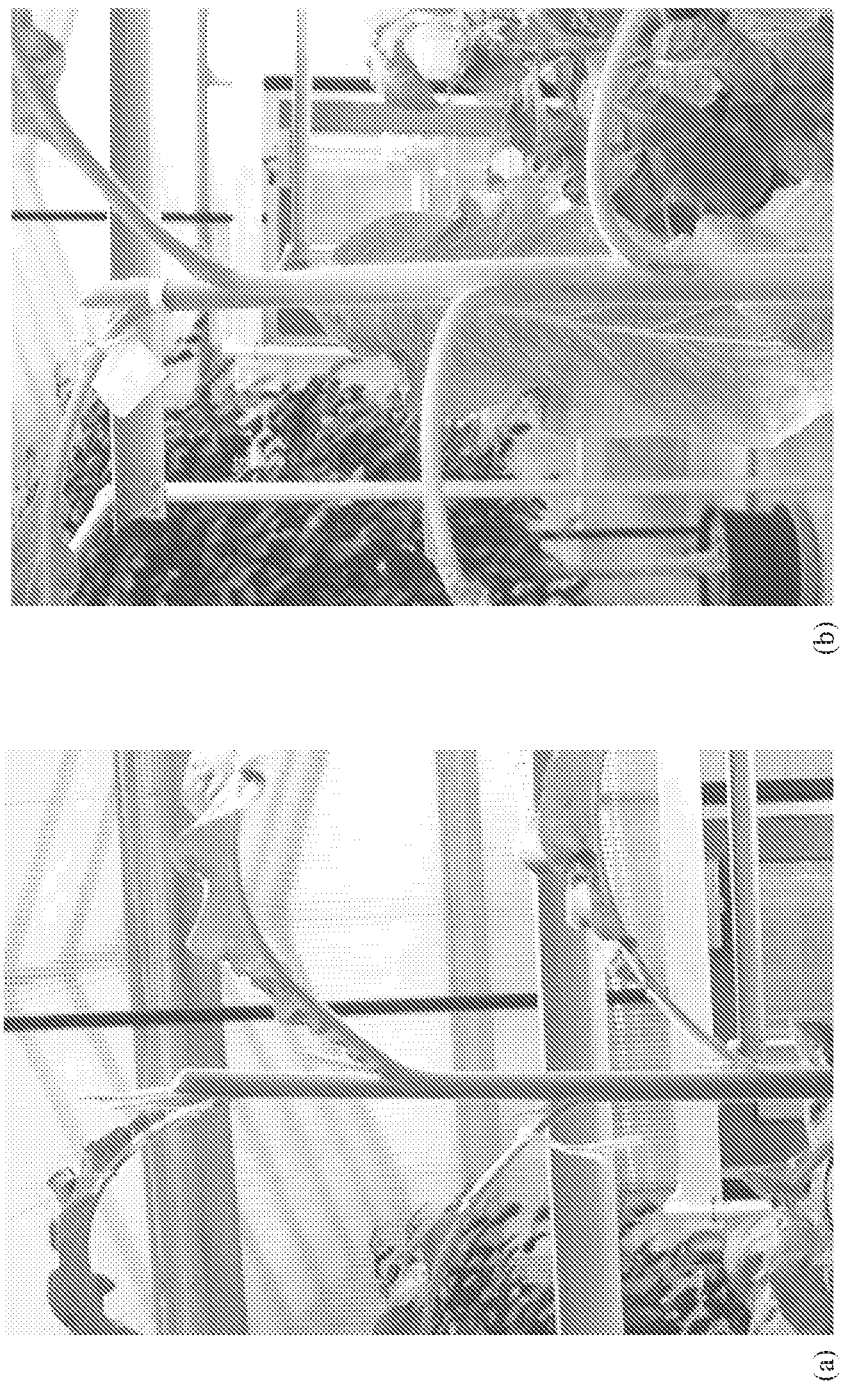
FIG. 5 shows the outgrowth of lateral shoots in tobacco upon topping, and the effect of transformation with ATC 085-PAP; (a) shows an untransformed control plant, showing elongated outgrowth of lateral shoots; (b) shows an ATC085-PAP transgenic plant showing no visible bud outgrowth.

FIG. 5 shows the reduced outgrowth of lateral shoots in ATC 085-PAP transgenic plants compared to control plants.

EXAMPLE 9

Characterisation of the ATC 085 Promoter-GUS Expression in *Arabidopsis* Plants

The construct pBNP085-0040-001 was used to transform *Arabidopsis thaliana* plants. Forty T1 plants were used for GUS analysis. The plants were grown in soil under long day conditions for 3-4 weeks until after floral transition when the primary axis had 'bolted' to a length between 20-40 mm. The plants were then decapitated by removing the main stem a point approximately 10 mm from the upper part of the rosette. They were then allowed to continue growing for 24 hours before being removed from soil, washed thoroughly in distilled water and assayed for GUS activity. GUS staining was conducted as described above for the tobacco plants, except that whole plants were used.

GUS expression was detected in the plants by highly intense staining at the base of the plant at the site of lateral bud formation and in the stem nearby. However, expression was also seen in other tissues in several of the plants, including the leaf tissues and veins, petioles, stem, and primary roots.

EXAMPLE 10

Characterisation of the ATC 023 Promoter-GUS Expression in Tobacco Plants

Forty-two tobacco plants transformed with the construct pBI101 023-0101-001 were grown in the greenhouse and treated as described above for GUS analysis.

GUS expression was detected in the lateral buds of 85% of the plants irrespective of the treatment (topped, wounded, or untreated), and most of the plants exhibited expression at every bud position sampled. In many cases localised expression was also seen in the stem close to the point of lateral bud initiation. Expression was also detected in other tissues in some plants, predominantly in the flower tissues, but occasionally in root, stem, leaf or petioles.

Figure 6:
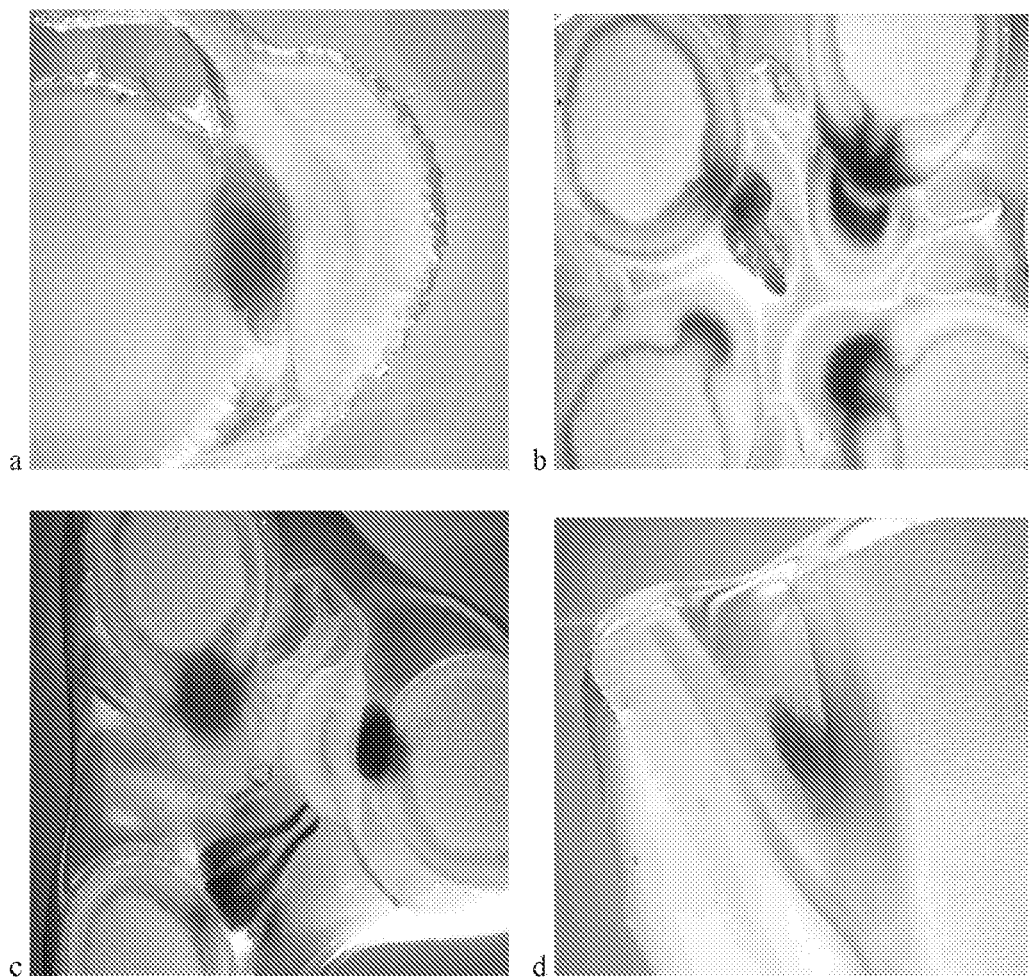
FIG. 6 shows the location of expression of the GUS reporter gene driven by the ATC 023 promoter in tobacco stem sections following topping. (a) shows a section through stem of one plant at the region of lateral bud initiation; (b) and (c) show serial sections through two lateral bud initiation regions taken from different plants; and (d) shows a vertical section through a leaf axil.

Specific localisation of expression to the lateral buds and the nearby stem was observed in 17% of the plants (FIG. 6). Hence the ATC023 promoter can be used alone to provide tissue specific expression. It can also be used in combination with another lateral bud expressing promoter, such as ATC 085, to provide complementary expression profiles with an overlapping site of action at the lateral bud tissue.

EXAMPLE 11

Characterisation of the ATC 023 Promoter-GUS Expression in *Arabidopsis* Plants

Five independent transgenic T2 lines carrying single inserts of the 023-0101-001 cassette were grown in soil, decapitated and stained for GUS analysis as described above.

Figure 7:
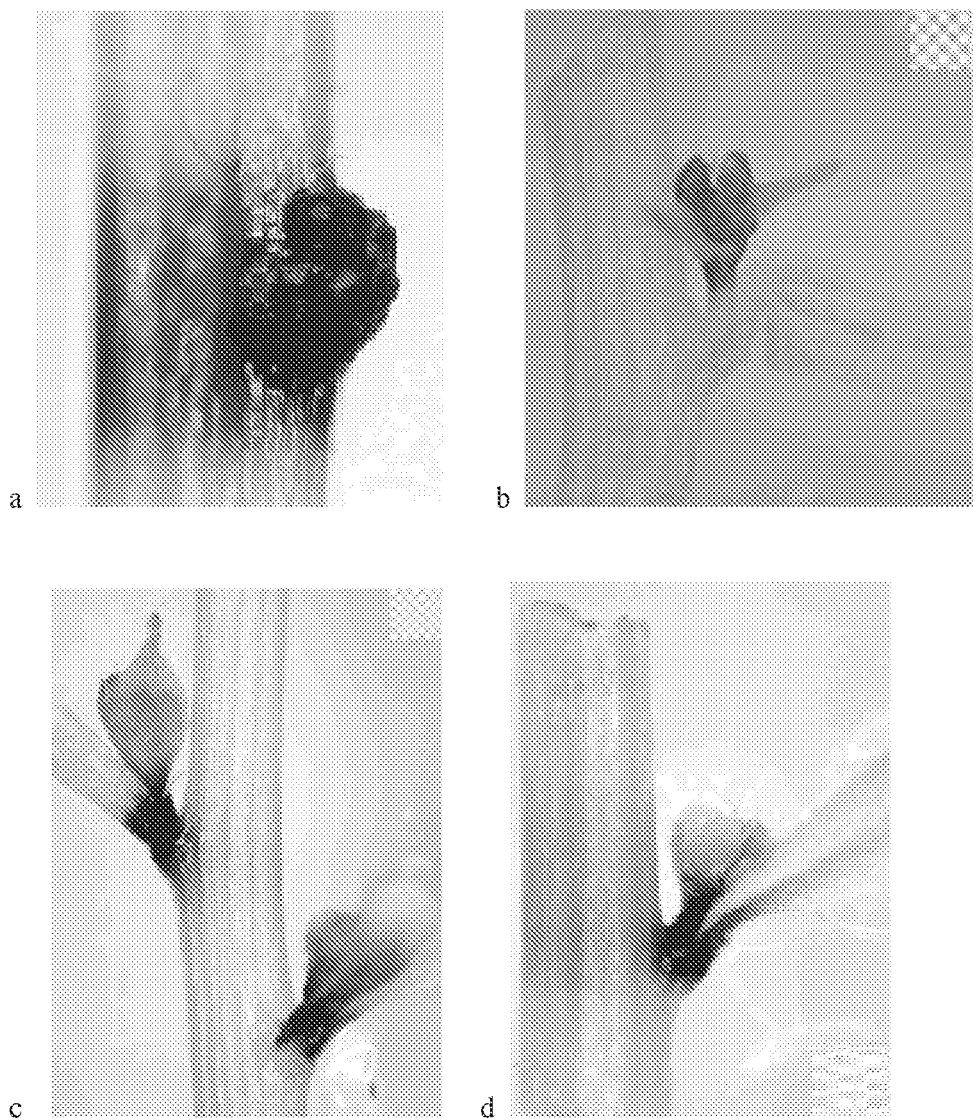
FIG. 7 shows the location of expression of the GUS reporter gene driven by the ATC 023 promoter in *Arabidopsis* stem sections. (a) shows expression at the point of bud outgrowth early in bud development, and (b)-(d) show subsequent expression in developing buds and nearby tissues.

GUS expression was observed in the axillary buds and adjacent stem, and floral tissues (FIG. 7). Expression associated with the smaller buds was the strongest, and decreased steadily as the buds developed. This indicates that the ATC 023 promoter is associated with lateral bud initiation. Some expression was also detected in other tissues in some plants, including the floral tissues.

All publications mentioned in the above specification are herein incorporated by reference. Various modifications and variations of the described methods and system of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Altschul, S. F., Madden, T. L., Schïffer, A. A., Zhang, J., Zhang, Z., Miller, W. and Lipman, D. J. (1997) Gapped BLAST and PSI-BLAST: a new generation of protein database search programs. Nucleic Acids Res. 25 3389-3402

Ausubel, F. M. Bent, R. Kingston, R. E. Moore, D. D. Seideman, J. G. Smith J. A. & Struhl K. (1989). Current protocols in molecular biology. New York: Greene and Willy Interscience.

Baxevanis, A. D. (2001). Predictive Methods using DNA Sequences. In "Bioinformatics: A Practical Guide to the Analysis of Genes and Proteins." Editors A. D. Baxevanis and B. F. Ouellette. John Wiley and Sons Inc., New York. Pp. 233-252

Becker et al, (1992) Plant Molec. Biol. 20 1195-1197

Benfey, P. N., and Chua, N-H. (1989) Regulated genes in transgenic plants. Science 244 174-181.

Bevan, M. (1984) Binary *Agrobacterium* Vectors for Plant Transformation. Nucleic Acids Research 12 8711-8721

Christensen, A. H. & Quail, P. H. (1996). Ubiquitin promoter-based vectors for which level expression of selectable and/or screenable marker genes in monocotyledenous plants. Transgenic Research 5 213-218

Clough, S. J. & Bent, A. F. (1998). Floral dip: a simplified method for *Agrobacterium*-mediated transformation of *Arabidopsis thaliana*. Plant Journal 16 735-743.

Cornejo M J, Luth D, Blankenship K M, Anderson O D, Blechl A E. (1993). Activity of a maize ubiquitin promoter in transgenic rice. Plant Molec. Biol. 23 567-81

Delaporta, S. L. Wood J. R. & Hicks, J. B. (1983). A plant DNA minipreparation: version 2. Plant Molecular Biology Reporter 1 19-22.

Devereux J, Haeberli P, Smithies O. (1984). A comprehensive set of sequence analysis programs for the VAX. Nucleic Acids Res. 12 387-95

Esau K. (1960) Anatomy of seed plants. New York & London. John Wiley & Sons Inc.

Gatz, C. (1995) Novel inducible/repressible gene expression systems. Methods in Cell Biol. 50 411-424

Horsch, R. B., Fry, J. E., Hoffman, N. L., Eichholtz, D., Rogers, S. G. & Fraley, R. T. (1985) A simple and general method for transferring genes into plants. Science 227 1229-1231.

Jefferson, R. A. (1987) Assaying Chimeric Genes in Plants: The GUS Gene Fusion System. Plant Molec. Biol. Reptr. 5 387-405

Kulikova T., Aldebert P., Althorpe N., Baker W., Bates K., Browne P., van den Broek A., Cochrane G., Duggan K., Eberhardt R., Faruque N., Garcia-Pastor M., Harte N., Kanz C., Leinonen R., Lin Q., Lombard V., Lopez R., Mancuso R., McHale M., Nardone F., Silventoinen V., Stoehr P., Stoesser G., Tuli M. A., Tzouvara K., Vaughan R., Wu D., Zhu W., and Apweiler R. (2004) The EMBL Nucleotide Sequence Database. Nucleic Acids Res. 32 D27-30

Mariani C, De Beuckeleer M, Truettner J, Leemans J, Goldberg R B (1990). Induction of male sterility in plants by a chimaric ribonuclease gene. Nature 347 737-741

Needleman S B, Wunsch C D. (1970) A general method applicable to the search for similarities in the amino acid sequence of two proteins. J. Molec. Biol. 48 443-53

Odell J T, Nagy F, Chua N H. (1985). Identification of DNA sequences required for activity of the cauliflower mosaic virus 35S promoter. Nature. 313 810-2.

Sambrook, J., Frisch, E. F. and Maniatis, T. (Eds.) (1989) Molecular Cloning: A Laboratory Manual, 2nd edn. Cold Spring Harbor Laboratory Press, New York.

Smith, T. and Waterman, M. S. (1981). Comparison of biosequences. Advances in Applied Mathematics, 2 482-489.

Stirpe, F. and Barbieri, T. (1986) Ribosome-inactivating proteins up to date. FEBS Lett. 195 1-8

Warner S A, Scott R, Draper J. (1993). Isolation of an asparagus intracellular PR gene (AoPR1) wound-responsive promoter by the inverse polymerase chain reaction and its characterization in transgenic tobacco. Plant J. 3 191-201.

Zhang W, McElroy D, Wu R. (1991). Analysis of rice Act1 5' region activity in transgenic rice plants. Plant Cell 3 1155-65

---

The invention claimed is:

1. A chimaeric gene comprising: a promoter sequence operably associated with a heterologous nucleic acid sequence, the promoter sequence comprising a sequence selected from the group consisting of: SEQ ID NO:4; a sequence having at least 95% identity with SEQ ID NO:4; and a sequence capable of hybridizing to SEQ ID NO:4 under stringent hybridization conditions, said stringent hybridization conditions comprising washing for 2×15 minutes with a 0.1×SSC, 0.5% SDS buffer at a temperature of 65° C.; and wherein the promoter sequence is operable to direct expression in at least one of a lateral bud and a lateral shoot.

2. The chimaeric gene according to claim 1, wherein the nucleic acid sequence encodes a cytotoxic molecule.

3. The chimaeric gene according to claim 1, wherein the nucleic acid sequence encodes a ribosome inactivating protein (RIP).

4. The chimaeric gene according to claim 1, wherein the nucleic acid sequence encodes a pokeweed antiviral protein.

5. The chimaeric gene according to claim 4, wherein the pokeweed antiviral protein (PAP) is pokeweed antiviral protein S (PAP-S).

6. A method of modifying morphology in a plant comprising introducing into a plant the chimaeric gene of claim 1 and wherein the nucleic acid sequence encodes a cytotoxic molecule.

7. The method according to claim 6, wherein the nucleic acid sequence encodes a ribosome inactivating protein (RIP).

8. The method according to claim 6, wherein the nucleic acid sequence encodes a pokeweed antiviral protein.

9. The method according to claim 8, wherein the pokeweed antiviral protein (PAP) is pokeweed antiviral protein S (PAP-S).

10. The method according to claim 6, wherein an outgrowth of at least one of a lateral bud and a lateral shoot is modified.

11. The method according to claim 10, wherein the outgrowth of at least one of the lateral bud and the lateral shoot is one of reduced, prevented and delayed.

12. The method according to claim 10, wherein the outgrowth of at least one of the lateral bud and the lateral shoot is modified by one of disrupting the metabolism and causing death of cells involved in lateral bud development.

13. A method of one of regulating the expression of a gene in a plant and modifying the metabolism within a cell of a transgenic plant, comprising introducing into a plant the chimaeric gene of claim 1 and wherein the nucleic acid sequence encodes a cytotoxic molecule.

14. A recombinant DNA comprising vector DNA and a promoter sequence operably linked to a heterologous nucleic acid sequence, wherein the promoter sequence is selected from the group consisting of: SEQ ID NO:4; a sequence having at least 95% identity with SEQ ID NO:4; and a sequence capable of hybridizing to SEQ ID NO:4 under stringent hybridization conditions, said stringent hybridization conditions comprising washing for 2×15 minutes with a 0.1×SSC, 0.5% SDS buffer at a temperature of 65° C.; and wherein the promoter sequence is operable to direct expression in at least one of a lateral bud and a lateral shoot.

15. A plant produced according to the method of claim 6.

16. A transgenic plant comprising the chimaeric gene as claimed in claim 1.

17. The plant according to claim 15, wherein the plant is of the family Solanaceae.

18. The plant according to claim 17, wherein the plant is of the subfamily Cestroideae.

19. The plant according to claim 18, wherein said plant is of the genus *Nicotiana*.

20. The plant according to claim 19, wherein said plant is *Nicotiana tabacum*.

21. The plant according to claim 15, wherein said plant is selected from the group consisting of tomato, cucumber, *Petunia, Dianthus, Picea, Pinus, Eucalyptus, Populus*, potato, tobacco, cotton, lettuce, eggplant, melon, squash, pea, canola, soybean, sugar beet sunflower, wheat, barley, rye, rice and maize.

22. A plant cell comprising the chimaeric gene as claimed in claim 1.

23. A plant cell comprising the recombinant DNA according to claim 14.

24. A synthesized nucleic acid comprising a promoter sequence comprising SEQ ID NO:4, further comprising a nucleic acid sequence encoding a cytotoxic molecule.

25. The synthesized nucleic acid of claim 24, wherein the nucleic acid sequence encodes a ribosome inactivating protein (RIP).

26. The synthesized nucleic acid of claim 24, wherein the nucleic acid sequence encodes a pokeweed antiviral protein (PAP).

27. The synthesized nucleic acid of claim 26, wherein the pokeweed antiviral protein (PAP) is pokeweed antiviral protein S (PAP S).

* * * * *

SEQUENCE LISTING

<160> NUMBER OF SEQ ID NOS: 9

<210> SEQ ID NO 1
<211> LENGTH: 1566
<212> TYPE: DNA
<213> ORGANISM: Nicotiana tabacum
<220> FEATURE:
<223> OTHER INFORMATION: promoter

<400> SEQUENCE: 1

```
gctatcaagc tttattaaag tgtccaataa gtgcaagcct attagttgaa atgtcaaaag      60
ttggtatcaa atttagggag ttatttatgc tcccgtttgg ccagatttcg gttactattt     120
tttaagttta atttgttttt tcaagtttca agatttatga cagttttga gtgatatttt      180 tccatttact cacaaaactt taactttttt ttttcaaata aaatacatgt acaaatacaa     240
ttttaatttt caaatattat tttccaacat aacttcaaaa actcttttttt caagtgttaa     300 ttaaatatat gtttaactat gtattcattt gtgcttatgt tttatcatgc attttcataa     360
gtgaatttca tactcatctt catgcaaaca cttatactat aaaagatata ttattcctat     420
atacaacatg tttatacgag atcattacat tgtaagtgta ccttattatt ggtaaatttt     480
ggacttcacc aaaaataatt aaggaagtaa tgatatgcaa taaataaata aataaataaa     540
gttaaaaata ttatacttga ctcaagacac attatgggga acacgwttct ttcacgatcc     600
atcttatcct ttcatcgata gaagttagca atagcattat tctcatatta gcggaattat     660
ggttgtttgt ctctttatat ggtcatagac tctcgagata attcatattt caagactagt     720 tatttttttag agctgaatta agtttaaaat ttatttcttc gttcgagcgt gcaagggtgt     780
taagcagggg ctgaggaaga gcattagtcg cgggttcgaa cgaactcagc ttaattctta     840
tatttgtatt agaaaataca taaatatgt ataaatatct aattacgaac ataataacta     900
agataaacta tgagttcctg ataaattgaa aatctataaa caccaaatcc tagctagtct     960
ctggtgttaa ggtgtcccac atttgttgag ggatggggttg ttatatggtc ttgggcaaga    1020
gttggagtca ctcggccacc aattatctat atttggccca ttgtttccca ttaaaacaat    1080
```

```
tcctcccaag ttgatctagt tactgttctc atttataatc caagttgata ctatttgtca    1140
tgtggctggc tatacgacat tgtttttgtt ttttttttgga aaatttctag gaaaccgtag    1200
ccgcttccat tcgggtgtgc atttgataac taactcactg tgcaattgct cgcaaatcac    1260
acagaagata taaatcgcat taggcacgcc cggtacgact agggggagac tactggtgag    1320
gagaatcgat ctcagatctc ccatatgata aaccactcac ccaactaact caatcaaccc    1380
cggcggcggg ygtgacttca cagtaagtct ttgtgaaggc tttcttttg tcattttctc    1440 ccttgtttag aacaagttgt tcttgcacga gaaactatta agtyatataa ataggggaga    1500
racattgttt cctttttac agcaaaaaat tgraactcca aatagctcat caaaggatcc    1560
tactcg                                                                1566

<210> SEQ ID NO 2
<211> LENGTH: 36
<212> TYPE: DNA
<213> ORGANISM: Artificial Sequence
<220> FEATURE:
<223> OTHER INFORMATION: PCR oligonucleotide S2CLOFWD

<400> SEQUENCE: 2
gctatcaagc tttattaaag tgtccaagct caagcc                               36

<210> SEQ ID NO 3
<211> LENGTH: 39
<212> TYPE: DNA
<213> ORGANISM: Artificial Sequence
<220> FEATURE:
<223> OTHER INFORMATION: PCR oligonucleotide S2CLEOREV

<400> SEQUENCE: 3
cgagtaggat cctttgatga gctatttgga gtttcaatt                             39

<210> SEQ ID NO 4
<211> LENGTH: 1904
<212> TYPE: DNA
<213> ORGANISM: Nicotiana tabacum
<220> FEATURE:
<223> OTHER INFORMATION: promoter ATC 023

<400> SEQUENCE: 4
cgaagacatt gtgtcgtaat cgtgtgtaat ttcactatct tccaaataaa gaaatataat     60
aattgcttct tgaatcggat gagctacacg ttttagata tttcgcaacc tgtcttcttc    120
gttagatcta ggaaacattg atttatagaa atatgtttct attatttctc tattattcat    180
tcaacatgtt aatatcgcca ccactcaaat atattgacca tgtcaattgt ttgattgaac    240
tataagtttg ataaacaatt gtcaaattta taaaaattta aaagagaaaa tgcatttata    300
tgaaagaaaa gaaaagtgca aaaagaaag aacaaaggat aaatgagagg tcgattttgt    360
ttaggaggat atggaattgc ttccaaattt agcaaagaaa cataaatgtt tttgccccta    420
taaagtcttt aaacgttatt ccaaatctgt tccaacatgt cctcttcatc cgacacattt    480
cttatcctct tctctaattt tttttgctaa aattaaatcg aaaattgaaa acgaattttt    540
gagaactatg taagatattt ttttttcttcc aataacaaca aattaccaaa caactttttg    600
tcgttttgtt actaaataag tggtacaatg aaattataag tgatacaata aaatcatttg    660
acttagatat aataatattc aaattaaaat gacaacaata cacaataaaa ttatgagaat    720
tcttcgaatc atatcaaaaa ttaatttttt ttttcgata caataaaatt attaaacaac    780
tttttgtcgt aagattattt tttcctgata acaataaatt attaaataat ttcgatcgt    840
```

```
tttgttgtta gataaatgat acaatgaatt catttcaaca acttagatac aacaatatttt    900 ggatcaaaat gaaaattata aacaaagtat catatatctt tgtatcatat caaaaacaag     960
atcatttttt ccgataacaa taaattatta aacaactttt tgtcgttttg ttgctagata    1020
agtgaaacaa taaaatcatt ttgacgaatt agatataaca atattaagat cacaatgaac    1080
aatagtaaac aacaaattat cagatatttt ggtattaaaa ataagattat ttttccgata    1140
ataacaaatt attaaacaat tttttttatag ttttgatgct aaataagtga tataatgaaa   1200
ttgttttgac gatttagaca caataatatt aggttcaaaa tgacaatact aaacaacaaa    1260
ttatcagatc atatcaaaaa taaaattatt tttttcgata acagcaaatt attaaacaac    1320 tttttttta ttgctagata aatgatacaa taacctcatt cgatatatat aataatattc     1380
aaatcaaaat gacaataata aacaataaat tattatattg aatcatataa aaaataagag    1440
atacatgcaa cgaataatta aacaaacaaa ttaagtaata aggcaatgga tagactaatt    1500
aatgaaacta aaactgtgga ttatctattt tgtcgtctttt cggagaatct aaacttcgac   1560
cgacttcaac gtatctaata atcctaaagt aaccttacgc tcacagttcg gttactttaa   1620
acttcgtcaa agtcattttg ataaacgtcc acatcacgaa acggtccacg tacgtctatc   1680
tcgtggataa gtctccagcc gctgtttcac atgcttatct cacagctttg ttacgataac   1740
ctagtcctat gctaatatct ttaaccatag ttaaataatt ttaaccaaac cacggttaag   1800
tgtttcaact acataagtag ctttgccggt gtattacaaa caacaacac aaacaaaaaa    1860 aaagaactct ttcgtcgact aatgtgattt attgttcacc ggat                     1904
```

<210> SEQ ID NO 5
<211> LENGTH: 31
<212> TYPE: DNA
<213> ORGANISM: Artificial Sequence
<220> FEATURE:
<223> OTHER INFORMATION: PCR Oligonucleotide AT4G29190L

<400> SEQUENCE: 5
ggcaagcttc gaagacattg tgtcgtaatc g                                    31

<210> SEQ ID NO 6
<211> LENGTH: 32
<212> TYPE: DNA
<213> ORGANISM: Artificial Sequence
<220> FEATURE:
<223> OTHER INFORMATION: PCR Oligonucleotide AT4G29190R

<400> SEQUENCE: 6
gcggatccgg tgaacaataa atcacattag tc                                   32

<210> SEQ ID NO 7
<211> LENGTH: 1541
<212> TYPE: DNA
<213> ORGANISM: Nicotiana tabacum
<220> FEATURE:
<223> OTHER INFORMATION: promoter ATC 085

<400> SEQUENCE: 7
tattaaagtg tccaataagt gcaagcctat tagttgaaat gtcaaaagtt ggtatcaaat     60
ttagggagtt atttatgctc ccgtttggcc agatttcggt tactattttt taagtttaat   120
ttgttttttc aagtttcaag atttatgaca gttttttgagt gatattttttc catttactca  180 caaaactttta acttttttttt tcaaataaaa tacatgtaca aatacaattt taattttcaa  240

```
atattatttt ccaacataac ttcaaaaact ctttttttcaa gtgttaatta aatatatgtt    300
taactatgta ttcatttgtg cttatgtttt atcatgcatt ttcataagtg aatttcatac    360
tcatcttcat gcaaacactt atactataaa agatatatta ttcctatata caacatgttt    420
atacgagatc attacattgt aagtgtacct tattattggt aaattttgga cttcaccaaa    480
aataattaag gaagtaatga tatgcaataa ataaataaat aaataaagtt aaaaatatta    540
tacttgactc aagacacatt atggggaaca cgtttctttc acgatccatc ttatcctttc    600
atcgatagaa gttagcaata gcattattct catattagcg gaattatggt tgtttgtctc    660
tttactatgg tcatagactc tcgagataat tcatatttca agactagtta tttttttagag   720 ctgaattaag tttaaaattt atttcttcgt tcgagcgtgc aaggggttta agcagggct    780 gaggaagagc attagtcgcg ggttcgaacg aactcagctt aattcttata tttgtattag    840
aaaatacata aaatatgtat aaatatctaa ttacgaacat aataactaag ataaactatg    900
agttcctgat aaattgaaaa tctataaaca ccaaatccta gctagtctct ggtgttaagg    960
tgtcccacat ttgttgaggg atgggttgtt atatggtctt gggcaagagt tggagtcact   1020
cggccaccaa ttatctatat ttggcccatt gtttcccatt aaaacaattc ctcccaagtt   1080
gatctagtta ctgttctcat ttataatcca agttgatact atttgtcatg tggctggcta   1140
tacgacattg ttttttgtttt ttttggaaaa tttctaggaa accgtagccg cttccattcg   1200
ggtgtgcatt tgataactaa ctcactgtgc aattgctcgc aaatcacaca gaagatataa   1260
atcgcattag gcacgcccgg tacgactagg gggagactac tggtgaggag aatcgatctc   1320
agatctccca tatgataaac cactcaccca actaactcaa tcaaccccgg cggcgggtgt   1380
gacttcacag taagtctttg tgaaggcttt cttttttgtca ttttctccct tgtttagaac   1440
aagttgttct tgcacgagaa actattaagt tatataaata ggggagaaac attgttttcc   1500
tttttacagc aaaaaattgg aactccaaat agctcatcaa a                       1541
```

<210> SEQ ID NO 8
<211> LENGTH: 1247
<212> TYPE: DNA
<213> ORGANISM: Nicotiana tabacum
<220> FEATURE:
<223> OTHER INFORMATION: Sar8.2b promoter

<400> SEQUENCE: 8

```
cttgtcttgt agtctattag cattgaggta catgtatcca agaacaaata aagtaatatt     60
gaagtatcta agagcaagcc tattagttga aatgacaaag gtaggtataa aattttggga    120
gttatttatg ctcccgtttg gccattgatt ttggctacta ttttttcaagt taaattcttt   180 tttcaacttc ccaaaaattg atttatgaca tttttttggat aaaagttttt ttccacctac   240
aaaatttaac ttctttttttt caaataaaat gcatgtccaa acacaacttc aactttcaaa   300
tatatttttt aacataactt caaaaactct ttttcaagt tttaattata catatgttca    360
actatgtatt catttctagt tatgtttatc acgcatttca taagtgaatt tcatacttat   420
cttcatgcaa acatatatac tataaaagat atattattcc taaatacaac atgtgatacg   480
agatcattac attgcaactg accttattat tttttaaattt tggacttcac caaaaatagt   540
tgggtttttt aatcgatttg atttaattttt tcggtttggt gcggttttcc gatttggttt   600
gaacacccct atcggtggt aaggtgtccc acatttgttg agggatgggt ggtactatgg    660
tcttgggcaa gagttggagt cactcggcca ccaattatct acgtcaagag ttggagtcac    720
tcgccaccaa ttatctacgt caagagttgg agtcactcgg ccaccaattg tctacatttg   780
```

```
gcccattgtt tcccattaaa acaattcgcc ctaagtaaac aatccaaatt gatacaattt    840
gtcaagtggc catgtaacga cattgttttt gttttttttct tggaaagttc ctagcaaacc    900
cgtagccact acccttcggg tgcgcacggg gtaattcgct cactgtatat tagctcacaa    960
attacacaag agatataaat cgcattaggt acacccgata tgacgaactc tgactgagga   1020
gactgctagt gagggaatcc atctcaggtt tcttatgtgg gaaatcactc gcccaactaa   1080
ctcagtctac cttggcgtgc gtgactttaa agtaagtctt ttgtgaaggc tttccttttt   1140
gtcatttttc tcccttgttc agagcaagtt gttctataaa tagggagaa acattatttc   1200 ccttttcaca gcaaaaaatt aaaactcgat atagctcatc tttcaaa              1247
```

<210> SEQ ID NO 9
<211> LENGTH: 3436
<212> TYPE: DNA
<213> ORGANISM: Arabidopsis thaliana
<220> FEATURE:
<223> OTHER INFORMATION: AT4g29190

<400> SEQUENCE: 9

```
tatgcatata ttaaatcgct ttcaatcaaa tttgtgtgcc ttgttttctt tataaaagaa     60
tacaattcag cctcgtagga gctgagctac gacattgaag atattttgg tccgtacgta    120 ttactatggt ttaataggtt aagtgactat gaaaacgaag acattgtgtc gtaatcgtgt    180
gtaatttcac tatcttccaa ataaagaaat ataataattg cttcttgaat cggatgagct    240
acacgttttt agatatttcg caacctgtct tcttcgttag atctaggaaa cattgattta    300
tagaaatatg tttctattat ttctctatta ttcattcaac atgttaatat cgccaccact    360
caaatatatt gaccatgtca attgtttgat tgaactataa gtttgataaa caattgtcaa    420
atttataaaa atttaaaaga gaaaatacat ttatatgaaa gaaagaaaa gtgcaaaaaa    480 gaaagaacaa aggataaatg agaggtcgat tttgtttagg aggatatgga attgcttcca    540
aatttagcaa agaaacataa atgttttgc ccctataaag tctttaaacg ttattccaaa    600
tctgttccaa catgtcctct tcatccgaca catttcttat cctcttctct aattttttttt    660 gctaaaatta aatcgaaaat tgaaaacgaa ttttttgagaa ctatgtaaga tatttttttt    720
cttccaataa caacaaatta ccaaacaact ttttgtcgtt ttgttactaa ataagtggta    780
caatgaaatt ataagtgata caataaaatc atttgactta gatataataa tattcaaatt    840
aaaatgacaa caatacacaa taaaattatg agaattcttc gaatcatatc aaaaattaat    900 ttttttttt cgataacaat aaattattaa acaacttttt gtcgtaagat tatttttttcc    960 tgataacaat aaattattaa ataatttcg atcgttttgt tgttagataa atgatacaat   1020
gaattcattt caacaactta gatacaacaa tatttggatc aaaatgaaaa ttataaacaa   1080
agtatcatat atctttgtat catatcaaaa acaagatcat tttttccgat aacaataaat   1140
tattaaacaa cttttttgtcg ttttgttgct agataagtga acaataaaa tcattttgac   1200 gaattagata taacaatatt aagatcacaa tgaacaatag taaacaacaa attatcagat   1260
attttggtat taaaataag attattttttc cgataataac aaattattaa acaatttttt   1320
tatagttttg atgctaaata agtgatataa tgaaattgtt ttgacgattt agatacaata   1380
```

```
atattaggtt caaaatgaca atactaaaca acaaattatc agatcatatc aaaaataaaa     1440
ttattttttt cgataacagc aaattattaa acaacttttt ttttattgct agataaatga     1500
tacaataacc tcattcgata tatataataa tattcaaatc aaaatgacaa taataaacaa     1560
taaattatta tattgaatca tataaaaaat aagagataca tgcaacgaat aattaaacaa     1620
acaaattaag taataaggca atggatagac taattaatga aactaaaact gtggattatc     1680
tattttgtcg tctttcggag aatctaaaact tcgaccgact tcaacgtatc taataatcct     1740
aaagtaacct tacgctcaca gttcggttac tttaaacttc gtcaaagtca ttttgataaa     1800
cgtccacatc acgaaacggt ccacgtacgt ctatctcgtg ataagtctc cagccgctgt      1860
ttcacatgct tatctcacag ctttgttacg ataacctagt cctatgctaa tatctttaac     1920
catagttaaa taattttaac caaaccacgg ttaagtgttt caactacata agtagctttg     1980
ccggtgtatt acaaacaaac aacacaaaca aaaaaaaaga actctttcgt cgactaatgt     2040
gatttattgt tcaccggagt attaaagaag atgatgatcg gagaaactcg caggacttat     2100
cccactgttg aaatacctcc atggccggta cttgaagagc ttacaacgtc ggagtttttt     2160
tctccggtga tgaatagtcc agattgtagc atgcttgaag ctttggcggg gttgcagcgt     2220
tatttgccgt ctaacgaacc ggatccggag tcatacccgg atctattggg tccggattca     2280
ccaatcgatg cttactcatg cgaccatttc cgtatgtacg atttcaaagt caggaggtgt     2340
gctcgtggcc ggagtcatga ttggacggag tgtccgtacg ctcatcccgg agaaaaagct     2400
cgccggagag atccgaggaa gtaccattac tctggtacgg cttgtcctga ttttcgtaaa     2460
ggtggctgca agaaaggtga ctcttgtgag tttgctcatg gtgttttcga gtgttggctt     2520
catccagctc gttaccgtac tcagccgtgt aaagacggtg gtaactgtct ccggaaaatt     2580
tgtttctttg ctcattcacc ggatcagctt aggttttac atactcggag ccctgacaga      2640
gttgattctt ttgacgtttc gtctccgatt cgtgctagag catttcagct gtcgatttct     2700
ccggtttctg gttcgccacc gatgagtcca agagctgact cggagtcttc tccgatgact     2760
cagtcactga gtcgatctct cgggtcttgt tcgataaacg acgtcgttcc ttcgtttagg     2820
aatttacagt ttaattcggt aaaatcattt cctcgtaaca atcctttatt cggattcggg     2880
tcgccccgtg gatcgatctt gggtcctggg tttcagtctc tgcctacaac accgacccga    2940
ccagggaatc tggatatttg ggagtatggt ttggaggaag aacccgtaat ggagcgtgtc     3000
gttgagtcgg gtcgtgagct acgagaaaag atgcgcgaga aactgcacaa ggagaattgc     3060
atggatcgag ttgcccagga tccggatcag aatttgggtg aggctcctga tgtcgggtgg     3120
gtatctgacc tgctcatgta aagaaaaaaa tctgaccgta tttcgaagtc tcattggctt     3180
ttttggatat cttccaagga aaagaggaag ggatcttagt gtgttcatat tattttattt     3240
actaatctcg tattttatct gctaataaga attaattatg gattttgggg cctgattttt     3300
ctaagatgat cgttgtatag atgtgcctta gggttttaat tatgaaatag tattaatata     3360
atcgtgtttt ataagactat aatgttagat tgtaaccact tggtactaat ctatgaatga     3420
atgcaaatta ttatct                                                      3436
```